United States Patent [19]

Nicolson et al.

[11] Patent Number: 5,030,559
[45] Date of Patent: Jul. 9, 1991

[54] METHODS AND COMPOSITIONS FOR THE IDENTIFICATION OF METASTATIC HUMAN TUMORS

[75] Inventors: Garth L. Nicolson, Kingwood; Susan M. North; Peter A. Steck, both of Houston, all of Tex.

[73] Assignee: Board of Regents, The University of Texas System, Austin, Tex.

[21] Appl. No.: 846,938

[22] Filed: Apr. 1, 1986

[51] Int. Cl.$^5$ .............. G01N 33/53; G01N 33/567; C07K 15/14; C07K 1/14

[52] U.S. Cl. .............. 435/7.23; 424/85.8; 435/69.3; 435/172.2; 435/240.27; 435/975; 436/501; 436/503; 436/536; 436/543; 436/547; 436/548; 436/64; 436/808; 436/813; 530/387; 530/395; 530/403; 530/413; 530/417; 530/828; 935/107; 935/110

[58] Field of Search .............. 436/501, 503, 543, 536, 436/548, 547, 813, 811, 64, 808; 435/172.2, 7, 240.27, 803, 810, 69.3; 530/387, 395, 403, 402, 407, 413, 828; 424/85; 935/107, 110

[56] References Cited

U.S. PATENT DOCUMENTS

| | | | |
|---|---|---|---|
| 3,697,638 | 10/1972 | Hansen | 436/813 |
| 4,140,753 | 2/1979 | Edgington et al. | 530/413 |
| 4,145,336 | 3/1979 | Edgington et al. | 530/387 |
| 4,289,690 | 9/1981 | Pestka et al. | 530/412 |
| 4,444,744 | 4/1984 | Goldenberg | 424/1.1 |

OTHER PUBLICATIONS

Sevier et al, Clin. Chem., vol. 27/11, 1981, pp. 1797-1806.
Neri et al. (1982), J. Natl. Cancer Inst., 68:507.
Parish et al. (1987), Int. J. Cancer, 40:511.
Sears et al. (1985), Can. Res., 45:5910.
Weiner et al. (1988), Can. Res., 48:2568.
Sindelar et al. (1986), Hybridoma, 5:5125.
Schroff et al. (1987), Jrnl. Biol. Resp. Mod., 6:457.
Steck et al., Chemical Abstracts, vol. 101, No. 1, p. 421, Jul. 2, 1984, Abstract No. 4877t.
Steck et al., Chemical Abstracts, vol. 106, No. 17, p. 492, Apr. 27, 1987, Abstract No. 136237x.
North et al., Biological Abstracts, vol. 83, (1987), Abstract No. 45662.
Ceriani et al., Chemical Abstracts, vol. 99, No. 11, p. 418, Sep. 12, 1983, Abstract No. 86294c.
Burchell et al., Journal of Immunology, vol. 131, No. 1, p. 508, Jul. 3.
European Search Report, dated 4/24/89.
North et al., Cancer Research 46, 6393-6399, Dec. 1986.
Johnston et al. (1985) Cancer Research, 45:1894-1900.
Martin et al. (1986) A.J.C.P., 86:10-18.
Johnston et al. (1986) Cancer Research, 46:6462-6470.
Klug et al. (1986) Int. J. Cancer, 38:661-669.
Paterson et al. (1986) Int. J. Cancer, 37:659-666.
Colcher et al., Chapter 5, "Potential Diagnosis and Prognostic Applications of Monoclonal Antibodies to Human Mammary Carcinomas", from: Monoclonal Antibodies and Cancer, G. Wright, ed., Marcel Decker, Inc. Immunology Series, vol. 23.
Codington et al. (1978), J. Natl. Cancer Inst., vol. 60, pp. 811-818.
Nuti et al. (1982), Int. J. Cancer, vol. 29, pp. 539-545.
Ceriani et al. (1983), Somatic Cell Genetics, vol. 9, pp. 415-427.
Nicolson et al. (1983), Understanding Breast Cancer, pp. 145-165.
Peterson et al. (1983), Cancer Research, vol. 43, pp. 4291-4296.
Steck et al. (1983), Experimental Cell Research, vol. 147, pp. 255-267.
Schlom et al. (1984), Cancer, vol. 54, Dec. 1 Supplement 1984, pp. 2777-2794.
Steck et al. (1984), Transplantation Proceedings, vol. XVI, No. 2 (Apr.), pp. 355-360.

Primary Examiner—Esther L. Kepplinger
Assistant Examiner—Florina B. Hoffer
Attorney, Agent, or Firm—Arnold, White & Durkee

[57] ABSTRACT

Disclosed are monoclonal antibodies which react with human tumor cells, particularly metastatic human tumor cells, but not with normal human tissues tested. The monoclonal antibodies are prepared against a 580 kilodalton glycoprotein antigen, designated gp580, which is isolated from either rat or human tumor cells. Methods for isolating the glycoprotein antigen are disclosed as well. Moreover, techniques are disclosed for utilizing these antibodies both in the detection and in the prevention of human tumor lesions.

29 Claims, 5 Drawing Sheets

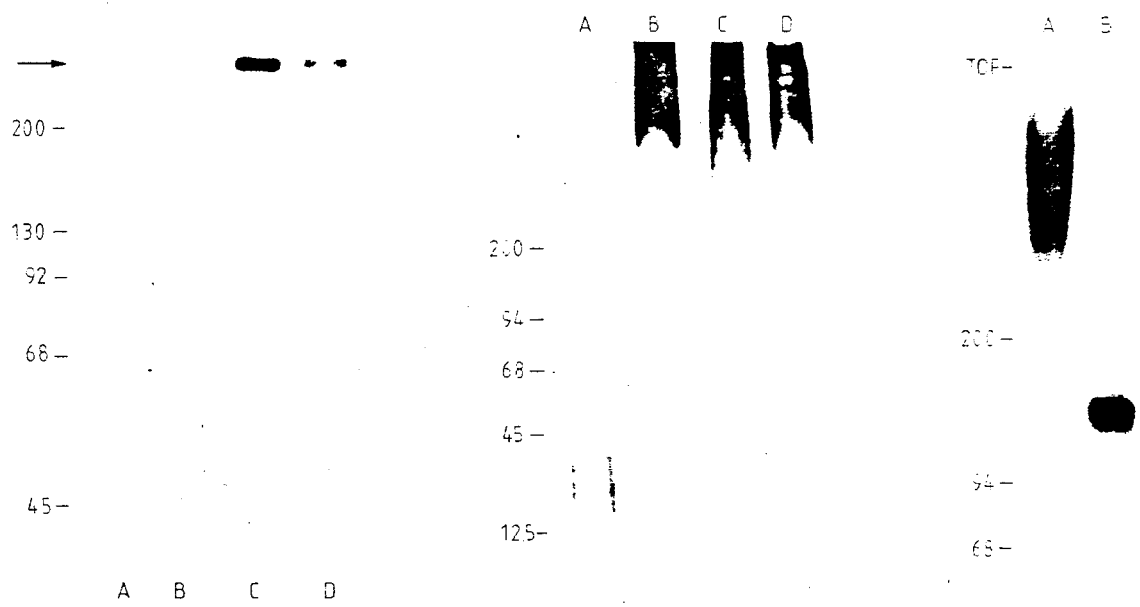

METHODS AND COMPOSITIONS FOR THE IDENTIFICATION OF METASTATIC HUMAN TUMORS

BACKGROUND OF THE INVENTION

1. Field of the Invention

The present invention is directed to methods and compositions useful in the detection of human tumor cells. More particularly, the invention is directed to antibodies, developed against either a 580 kilodalton rat or human glycoprotein antigen, as potentially valuable tumor immunodiagnostic reagents, and further, as useful reagents in the prevention of metastatic lesions.

2. Description of the Relevant Art

Breast cancer constitutes a leading cause of deaths to women in North America and Northern Europe. Although recent advances have significantly improved the rates of detection and eradication of primary breast cancers, a large percentage of breast cancer patients will develop metastatic lesions and eventually die.

The process of tumor metastasis occurs by means of a number of sequential and highly selective steps. Many of these steps require a number of complex interactions between the tumor cells and host environment, and the majority of these interactions appear to be mediated by cell surface components. To investigate the possible functional roles of certain cell surface components in the metastatic process, various researchers have correlated the expression or enzymatic activities of these components with the metastatic potential of tumor cell subline or clones. Alternatively, the surfaces of tumor cells have been modified metabolically or enzymatically and the metastatic properties of the modified cells examined.

For example, cell surface components of spontaneously metastasizing rat mammary adenocarcinoma have been previously examined for possible biochemical markers which may be associated with mammary tumor metastasis in the rat. A system which has been found to be a useful model for rat mammary tumor metastasis is the rat 13762NF mammary adenocarcinoma described in Neri et al. (1982), *J. Natl. Cancer Inst.*, 68: 507-517. Various cell clones and lines obtained from the 13762NF system were found to differ in their abilities to spontaneously metastasize to regional lymph nodes and distant organs. Additionally, they exhibit differences in cell and tissue morphologic appearance, karyotypes, and responses to therapeutic agents.

The expression of particular cell surface glycoproteins were found to correlate with the metastatic capabilities of these cells. For example, sialoglycoproteins having molecular weights between 175,000 and 250,000 are expressed on metastases-derived cells, while the major sialoglycoproteins have molecular weights between 80,000 and 120,000 in cells derived from a primary rat tumor. A sialoglycoprotein having a molecular weight of approximately 80,000 was reduced in expression in more metastatic rat tumor cells; another glycoprotein having a molecular weight of approximately 580,000, synthesized by rat tumor cells, was increased in expresssion in the more highly metastatic rat tumor cells. However, no metastasis-associated 580 kilodalton glycoprotein has previously been identified in, or found to be associated with, human tumor cells.

The identification of human tumor-associated antigenic proteins on human tumor cell surfaces could lead to the production of antibodies which ar capable of immunodiagnosing human tumor cells. Unfortunately, many human tumor cells surface components are either poorly or non antigenic, or are also associated with various normal human tissues. Where cell surface antigens are common to both normal and tumor cells, immunodiagnostic probes directed against such antigens are unsatisfactory in that they exhibit a high number of falsely positive reactions.

Cancer immunodiagnostic probes have heretofore been imprecise in that they either detect high numbers of falsely positive reactions and/or falsely negative reactions. Accordingly, a tumor diagnostic probe exhibiting a high degree of correlation with the human cancerous state would be useful in the early diagnosis and treatment of human tumors. Additionally, an immunodiagnostic probe which correlates with metastatic tumors, would be similarly useful to the treating oncologist or surgeon.

SUMMARY OF THE INVENTION

In its most general and overall scope, the present invention provides compositions useful in identification of metastatic human tumor cells which include antibodies, both polyclonal and monoclonal, prepared against a 580 kilodalton glycoprotein tumor antigen, designated gp580. One form of the gp580 antigen found to be isolatable from rat tumor cells, in particular, rat mammary carcinoma cells, has been designated rgp580; a related antigen, which is chemically distinguishable from rgp580, has been isolated and characterized from a human tumor source, the antigen being designated hgp580. As used herein, the term "isolatable" designates that the particular antigen may be characterized as being isolatable from a particular source. However, this designation is not meant to imply that such source is the only source for isolation of the antigen so-designated.

The gp580 antigens of the present invention are glycoproteins having a molecular weight identifiable upon gel electrophoresis of approximately 580 kilodaltons. As used herein, the term "identifiable" designates that the gp580 antigen will exhibit an approximate molecular weight of 580 kilodaltons when subjected to gel electrophoresis under conditions similar to those specified herein. However, as will be appreciated by those of skill in the art, such size determinations are by no means exact and that alterations or variations in molecular sizing techniques may result in variations in the size exhibited by a particular antigen.

In a preferred embodiment, the antibody is a monoclonal antibody prepared by standard techniques well-known to those skilled in the art. Such monoclonals are preferably prepared by fusion of immunized rat spleen cells to rat myeloma cells. However, it is contemplated that full advantage of the present invention may be realized by fusion of other cell types, including those of murine origin.

It is a further object of the present invention to provide a hybrid continuous cell line producing antibodies reactive to hgp580 antigen or rgp580 antigen obtained through a process which includes the steps of fusing mammalian spleen cells with myeloma cells derived from an homologous species, wherein the organism providing the spleen cells has been immunized with an antigenic mixture comprising a gp580 antigen; culturing the cells in a selective medium; testing for the presence of the desired antibody; and cloning cells producing the desired antibody. Hybrid continuous cell lines producing antibodies reactive to human hgp580 antigen may be generated using spleen cells which have been immunized against either hgp580 or rgp580 antigen, in that such antibodies have been found to cross-react.

Essentially pure tumor gp580 antigens, useful in the production of human tumor-directed antibodies, are prepared by a process which includes the steps of extracting soluble proteins including gp580 from a tumor which contains the gp580; subjecting the extractate to gel exclusion chromatography; collecting the excludate; subjecting the excludate to anionic exchange chromatography; eluting the fractions which bind to the anionic exchange resins; subjecting the eluant to gel exclusion chromatography; and collecting the excluded fractions. Those with skill in the art will recognize that many variations exist to protein isolation techniques.

Essentially pure rpg580 antigen, also useful in the production of human tumor-directed antibodies, may be prepared in a similar fashion. Additionally, gp580 may be prepared by a process which includes the steps of extracting solubilized proteins including the gp580 from a rat or human tumor which contains the antigen; subjecting the extractate to gel exclusion chromatography; collecting the excludate; subjecting the excludate to density gradient centrifugation; fractionating the equilibrated density gradient; subjecting the gp580-containing fractions to gel exclusion chromatography; and collecting the excluded fractions. This process includes the additional step of density gradient centrifugation, which has been determined not to be crucial in the preparation essentially pure gp580 antigens.

It is further object to the present invention to provide a diagnostic method for detecting the presence of metastatic human tumor cells in the sample which includes the steps of contacting the sample with an antibody having a specificity for either the hgp580 or rgp580 antigen, and detecting materials bound by the antibody. Full advantages of this method may be realized by admixing the sample with the antibody under conditions which will promote specific antigen/antibody interactions and detecting the antigen/antibody interaction. It is contemplated that such diagnostic methods are generally applicable to samples which are derived from numerous biological sources, including but not limited to blood, plasma, milk, breast secretions, urine, saliva, perspiration, serum and tissue samples.

It is a further object of the present invention to provide a diagnostic method for detecting the presence of metastatic human tumor cells in a non-aqueous sample which includes the steps of layering the sample with a rgp580 or hgp580 antibody; incubating the layered sample under conditions which will promote specific antigen/antibody interactions; and detecting the antigen/antibody interaction.

It is a further object of the present invention to provide a method for reducing the frequency of metastatic lesions in cancer patients which includes administering to the patient an effective amount of a composition comprising an antibody to a gp580 antigen.

BRIEF DESCRIPTION OF THE DRAWINGS

FIG. 6. SDS-PAGE of radiolabeled and purified fractions. Panel A, [$^3$H]glucosamine-labeled Sephacel DEAE-cellulose fractions I through IV corresponding to lanes A through D. Panel B, [C]$^{14}$C]serine labeled purified gp580 (lane A), and trifluoromethylsulfonic acid-treated gp580 (lane B) are shown. Electrophoresis was performed on a 2 to 17.5% DATD acrylamide gel followed by fluorography. The protein standards include myosin, phosphorylase a, bovine serum albumin, and ovalbumin, with $M_r (\times 10^3)$ of 200, 94, 68, and 45, respectively.

DETAILED DESCRIPTION OF THE PREFERRED EMBODIMENTS

Figure 2B:
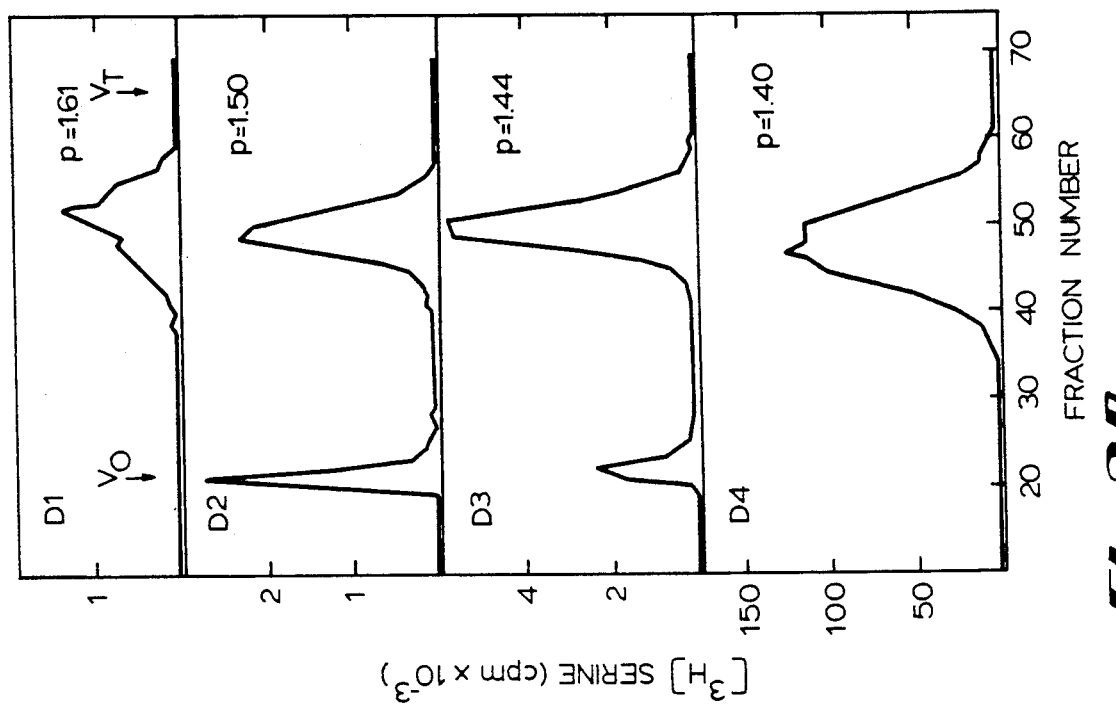
FIG. 2. Gel filtration of radioactively labeled macromolecules synthesized by MTLn3 cells after dissociative CsCl density-gradient ultracentrifugation. A, [$^3$H]Glucosamine- (—) and [$^{35}$S]sulfate-( .... ); and B,[$^3$H]serine-labeled cellular extracts from the various density gradient fractions were subjected to Sepharose CL-2B column chromatography in 4M guanidine HCl (GdnHCl) and 0.1M sodium acetate, all at pH 5.8. The average density of the fractions are denoted (p values), and the arrows represent the void volume ($V_0$) and total volume ($V_T$) elution fractions of the columns.

In its most general and overall scope, the present invention is directed to human tumor immunodiagnostic reagents which are useful in the identification and diagnosis of cancer and more particularly, to the diagnosis of metastatic cancer in humans. Additionally, the present invention is directed to therapeutic compositions useful in the prevention and treatment of metastatic disease. It has been determined that monoclonal antibodies prepared against a rat tumor cell surface glycoprotein, designated rgp580, or a human tumor cell surface glycoprotein, designated hgp580, are useful human tumor diagnostic reagents. Moreover, therapeutic compositions which include such antibodies have been found to inhibit the development of metastatic lesions.

Although the rat rgp580 protein has been previously shown to be expressed on the cell surfaces of various rat tumors, it has never been shown to be antigenic. Similarly, no 580 kilodalton glycoprotein has ever been found associated with human tumor cells. Therefore, the present invention discloses the unique finding that antibodies directed against the rat tumor antigen rgp580 can successfully immunodiagnose human tumors. Additionally, the present invention discloses antibodies directed against a previously undescribed human 580 kilodalton glycoprotein antigen that is similarly useful in the immunodiagnosis of human cancer. Both of the disclosed types of antibodies appear to react strongly with metastatic human mammary tumors.

The present invention is disclosed in terms of techniques determined by the inventors to be particularly useful in the 1) isolation and partial purification of the rgp580 antigen; 2) preparation of monoclonal antibodies with specificity for the rgp580 antigen; 3) isolation and partial purification of the hgp580 antigen; and 4) preparation of monoclonal antibodies with specificity for the hgp580 antigen. The antigen purification steps have been designed to take advantage of the antigens' relatively large molecular weight, their buoyant density relative to other proteins and their electrostatic charges relative to other proteins. Monoclonal antibodies were prepared utilizing both rat/rat and mouse/mouse fusions, with rat/rat hybrids being preferred.

Experiments performed by the present inventors have demonstrated the potential utility of the anti-gp 580 antibodies both in the detection of cancer, as an immunoscreening antibody, and in the possible prevention and treatment of cancer. The immuno-detection techniques disclosed herein are unique in that they utilize unique antibodies with unique specificities for proteins previously unknown to be antigenic and previously unknown to be associated with human tumors. However, the basic immunoscreening technology is well known to those skilled in the art.

In its most general embodiment, immuno-screening involves bringing a gp580 antibody into contact with a sample suspected of having either tumor cells, or tumor cell products (i.e. tumor antigens), associated with it. Therefore, a positive immunoreaction between a suspected sample and the gp580 antibody would be indicative of the presence of cancer cells in the organism from which the sample was derived. Numerous techniques for detecting a positive immunoreaction are known in the art including radioactive labels, color-producing substrates activated by enzymes (e.g. peroxidase) linked to either the antigen or antibody, radioimmunoassays (RIA's), enzyme-linked immunosorbent assays (ELISA's), or other ligands bound to the antigen or antibody, such as ferritin or avidin/biotin.

It is also contemplated that gp580 antigens of the present invention may prove useful as cancer-screening reagents themselves. For example, such antigens may be incorporated into an appropriate ELISA to detect for the presence of circulating anti-gp580 antibodies in a patient's serum, the presence of such circulating antibodies being indicative of cancer. Techniques for utilizing antigens to detect circulating antibodies are generally well known in the art.

Experiments performed by the inventors have demonstrated that antibodies of the present invention are useful in the prevention of cancer, particularly in the prevention of metastatic disease. This is thought to be a novel finding with respect to antibody reagents and suggests new approaches to the prevention of cancer. It is envisioned that such antibody preparations may be useful, for example, in treating post-operative cancer patients to prevent the occurrence of secondary or metastatic lesions which are thought to be a possible surgery-related complication. Such preparations could be given by intravenous infusion for a period of days, for example, following such surgery.

Alternatively, antibody preparations of anti-gp580 could be linked to toxigenic molecules, such as cholera, ricin, abrin, or modeccin toxin, to produce specific "killer" antibodies. Such toxin-conjugated antibodies would thereby have both specificity for the targeted tumor cells and the ability to kill such cells once targeted. Such antibodies would therefore have both the ability to seek out and destroy tumor cell populations and to prevent the development of such populations in the first place.

It is contemplated that antibodies of the present invention may be provided in the form of a cancer-screening kit. Such kits would include the appropriate anti-gp580 antibody together with an immunoreaction detection reagent. As used herein, an immunoreaction detection reagent is a reagent capable of indicating or detecting a specific immunoreaction between the antibody and the gp580 antigen. Examples of such reagents include peroxidase-tagged or radiolabeled antigens or antibodies. Such reagents, and their use, are well known to those skilled in the art.

EXAMPLE I

Isolation and Characterization of Rat rgp580

The rat 580 kilodalton glycoprotein, rgp580, may be isolated from numerous rat tumors or rat tumor cell lines. In fact, any rat tumor found to cross-react with the anti-rgp580 rat antibody, will serve as a starting source for the isolation of this rat tumor antigen. However, the present inventors have determined that a preferred source of rgp580 is rat mammary adenocarcinoma cells in that these cells appear to have a high level of rgp580 associated with their membranes. One cell line in particular, rat 13762NF tumor cell clone MLTn3, is utilized as a preferred source. Such cells were cloned from spontaneous lung metastases as described by Neri et al (1982), *J. Natl. Cancer Inst.*, 68; 507–157. However, those of skill in the art will also understand that other cell lines may be identified in the future which will prove to be better sources for rgp580.

Figure 1:
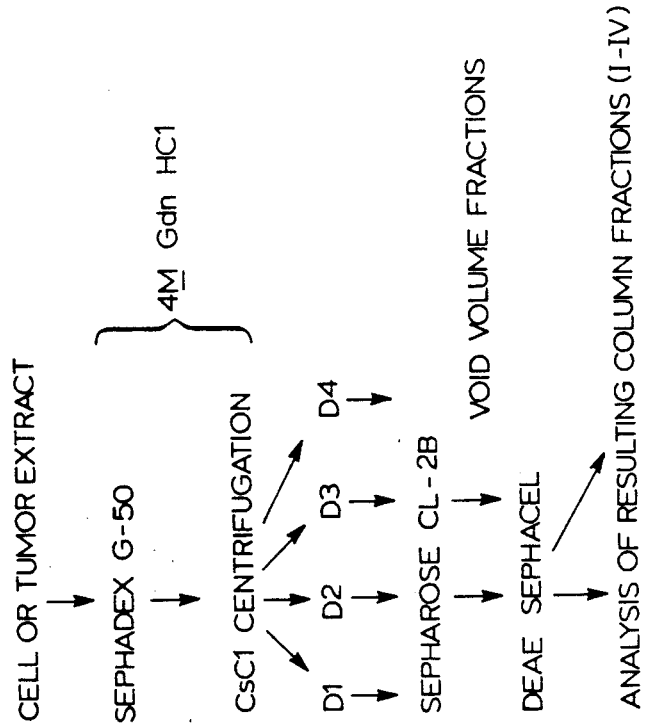
FIG. 1. Schematic diagram of the procedures used in the isolation of rgp580.

FIG. 1 is a schematic diagram of the procedures, described in more detail below, used in the isolation of rgp580. Briefly, after extraction of soluble proteins from an appropriate tumor cell, the extract is passed over a Sephadex G-50 column and the voided fractions are collected. The pooled void fractions are then centrifuged in a CsCl buoyant density gradient followed by Sepharose Cl-2B chromatography. The Sepharose Cl-2B fractions are then applied to a DEAE Sephacel column, eluted with NaCl; and fractions analyzed for the presence of rgp580.

a. Chemicals

The following chemicals represent a partial list of exemplary reagents employed in both the isolation of rgp580 and its characterization. However, those of skill in the art will recognize that numerous suitable replacements can be employed without departing from the scope of the invention. D-[6-$^3$H] glucosamine (20 to 30

Ci/mmol), D-[1-³H] galactose (1 to 5 Ci/mmol), L-[6-³H] fucose (20 to 35 Ci/mmol), L-[4,5-³H] leucine (30 to 50 Ci/mmol), L[6-³H] serine (5 to 10 Ci/mmol), L-[U-¹⁴C] serine (135 to 165 mCi/mmol) and [³⁵S] Na$_2$SO$_4$ were purchased from ICN Pharmaceuticals (Irvine, Calif.); D-[2-³H] mannose (10 to 20 Ci/mmol) was from New England Nuclear (Boston, Mass.); Streptomyces hyaluronidase and chondroitinase ABC were from Miles Laboratories (Elkhart, Ind.); collagenase type VII was from Sigma Chemical Co. (St. Louis, Mo.); trypsin (crystallized three times) was from Worthington (Freehold, N.J.); pronase was from Calbiochem (San Diego, Calif.); Alpha modified eagle's medium (AMEM) was from GIBCO (Grand Island, N.Y.); fetal bovine serum (FBS) was from Sterile Systems (Logan, Utah); and cesium chloride was from Bethesda Research Laboratories (Rockville, Md.).

b. Cells

The rat 13762NF tumor cell clone MTLn3 of high metastatic potential exhibits high levels of rgp580 and is therefore a preferred source for its isolation. Cells utilized for the isolation were cloned from spontaneous lung metastases as described in Neri et al. (1982), *J. Natl. Cancer Inst.*, 68: 507–517, and stored as frozen stock. MTLn3 cells were grown at 37° C. in a 5% CO$_2$-humidified air mixture on 100 mm tissue culture plates (Corning Glass, Corning, N.Y.) in AMEM media containing 10% FBS and no antibiotics. The cells used in this example were in exponential growth phase and were from in vitro passages T14 to T20. Cells were routinely screened and found to be free of mycoplasmal and viral contamination by the method of Chen (1976), *In Vitro*, 3: 229–232.

Mammary tumors were obtained by subcutaneous injection of approximately 1×10⁶ viable MTLn3 cells into the inguinal mammary fat pad of lightly anesthetized syngeneic female Fischer 344 rats (Charles River Breeding Laboratories, Portage, Mich.). This procedure resulted in a tumor with a diameter of 11.7±4.6 mm 30 days after injection of the tumor cells with 100% and 50% of tumor-bearing animals with lymph node and pulmonary metastatic lesions, respectively. Because the center of the tumor was necrotic at 30 days, the majority of tumors used were harvested at 14 days. For tumor harvesting, the rats were killed by inhalation of Metofane (Pitman-Moore, Inc., Washington, N.J.), and the tumors were carefully removed from the surrounding tissues, rinsed in phosphate-buffered saline (PBS), and minced. The pieces of tumor were then extracted as described below.

c. Radioactive Labeling of Tumor Cells

Metabolic radiolabeling of in vitro grown cells was utilized to radioactively label the rgp580 antigen. In general, this was conveniently accomplished by growing the cells in complete medium (AMEM plus 10% FBS; 5 ml in a 100 mm culture plate) containing 10 μCi/ml of [³H] glucosamine [³H] galactose, or [³H] fucose for 24 hours to label the carbohydrate moieties. In experiments in which cells were labeled with [³H] mannose, 200 μCi/ml was found to be sufficient when added to complete medium in which the AMEM contained one-half of the normal concentration of dextrose (1 gram/liter). To prepare cells labeled with [³H] leucine, [¹⁴C] serine, or [³H] serine, the medium contained 10 μCi/ml of the radioactive precursor and one-tenth the usual concentration of the amino acid (5.25 mg/l and 2.5 mg/l, respectively). The MTLn3 cells were labeled with 50 μCi/ml of Na$_2$[³⁵S]O$_4$ in AMEM in which the MgSO$_4$ (80.9 mol) was replaced with MgCl$_2$. After the 24 hour labeling period, the medium may be collected, centrifuged at 4° C. for 10 minutes at 2,000×g to remove cellular debris, and frozen at −80° C. The culture plates were washed twice with PBS and rgp580 extracted from the cells as described below.

Isolation of rgp580 from Metabolically-Labeled Tumor Cells

Cells which have been metabolically labeled with radioisotopes may be utilized in the isolation of rgp580 to provide a means of monitoring the isolation and purity as described above. The labeled protein migrates near the void volume of Sepharose CL-4B columns. Additionally, rgp580 binds ¹²⁵I-labeled peanut agglutinin after desialylation and that desialylated rgp580 can be identified after SDS polyacrylamide gel electrophoresis (SDS-PAGE) as a high molecular weight PNA-binding glycoprotein. These two techniques, described more fully below, were used to monitor the purification of rgp580 from both cultured MTLn3 cells and MTLn3 tumors.

The extraction of rgp580 is accomplished by first solubilizing the cells (0.5×10⁶ cells per dish) in extraction buffer (1 ml per five dishes of 4% Zwittergent 3-12, 4M guanidine HCl, 0.1M 6-aminohexanoic acid, 10 mM Na$_2$ EDTA, 5 mM phenylmethysulfonylfluoride, 5 mM benzamidine-HCl, 10 milliunits/ml aprotinin and 0.1M sodium acetate; pH 6.0). The plates were scraped, extracts combined and the solubilization continued at 4° C. for 18 hours with stirring. There was no apparent increase in the release of high molecular weight [³H] glucosamine- or [³H] serine-labeled material from the cells if they were sequentially extracted with 8% Zwittergent followed by addition of 8M guanidine HCl (GdnHCl) (both with protease inhibitors). The extracts which are preferably filtered over Whatman 1 paper are applied to Sephadex G-50 columns to remove low molecular weight solutes, and the void volume fractions pooled.

The pooled excluded fractions from the Sephadex G-50 columns were prepared for isopycnic dissociative density gradient centrifugation by mixing in 0.55 g cesium chloride (CsCl) per gram of solution and centrifuged at 9° C. for 48 to 72 hours at 35,000 rpm in either a Beckman SW 50.1 or TI 50.2 rotor. The gradients were divided into 8 equal fractions, and the density and radioactivity, if any, of each fraction were determined. The fractions were then pooled to give 4 equal-volume fractions designated D1 to D4, and each fraction was then analyzed by gel filtration chromatography. Certain radiolabeled aliquots of purified rgp580 were subjected to isopycnic centrifugation by mixing [¹⁴C] labeled rgp580 (1×10⁴ cpm) with 4M GdnHCl and 4.3M CsCl (or 0.5M GdnHCl and 6.5M CsCl) in 10 mM Tris, all at pH 7.2. The samples were centrifuged at 4° C. for 60 hours at 35,000 rpm in a Beckman SW50.1 rotor and then separated into 20 equal fractions.

The four equal volume cesium chloride fractions, D1 to D4, have found to decrease in cesium chloride concentration from 1.58 g/ml for D1 to 1.37 g/ml for D4. Aliquots of the various density fractions were dialyzed, lyophilized and subjected to SDS-PAGE for the identification of the major proteins contained in each fraction. The glycoproteins in the gels may be desialylated by mild acid treatment by the method of Burridge, K.

(1976), *Proc. Natl. Acad. Sci. USA*, 77: 4457–4481, and the gels were stained with $^{125}$I-labeled PNA. The rgp580 was detected mainly in the D2 fraction (P=1.48±0.03 g/ml) with some small amounts in the D1 and D3 fractions. Approximately 50% of the [$^3$H] glucosamine-, but less than 8% of the [$^3$H] serine-labeled macromolecules was found in fractions D1 to D3.

Portions of the D1 to D4 fractions were applied to calibrated Sepharose CL-2B column (115×0.8 cm), equilibrated with 4M GdnHCl in 0.1M sodium acetate, pH 5.8. The radioactivity of each fraction was determined by adding 200 ul of ethanol to 100-ul aliquots of fractions that were then added to 3 ml of LiquidScint (National Diagnostics; Somerville, N.J.). The fractions were pooled, dialyzed extensively against water, and then lyophilized. Certain pooled fractions were redissolved in 8M urea, 0.2% CHAPS, in 50 mM Tris-HCl, pH 7.2, and applied to a DEAE Sephacel column (5×1 cm) in the same buffer. The column was washed and eluted with a linear sodium chloride gradient of 0 to 1M. After the completion of the gradient, the column was washed with 8M urea containing 3M sodium chloride. Radioactivity recovery was greater than 90%. The fractions were pooled according to their radioactivity, dialyzed against water and lyophilized. The fractions were analyzed as described below. Some fractions were further fractionated on Sepharose CL-2B columns (115×0.8 cm) equilibrated and eluted with 1% SDS and 5 mM B-mercaptoethanol in 10 mM Tris-HCl.

The Sepharose CL-2B columns were standardized by using dextrans ($M_r$=2×10$^6$, 5×10$^5$, 1.5×10$^5$, 7×10$^4$, respectively). Samples used for carbohydrate analysis were applied to such a BioGel PG column (115×0.8 cm) equilibrated with 50 mM pyridium acetate, pH 5.3. The columns were standardized with oligosaccharides prepared from fetuin, as described by Spiro and Bhoyroo (1974), *J. Biol. Chem.*, 249: 5709–5717.

Figure 2A:
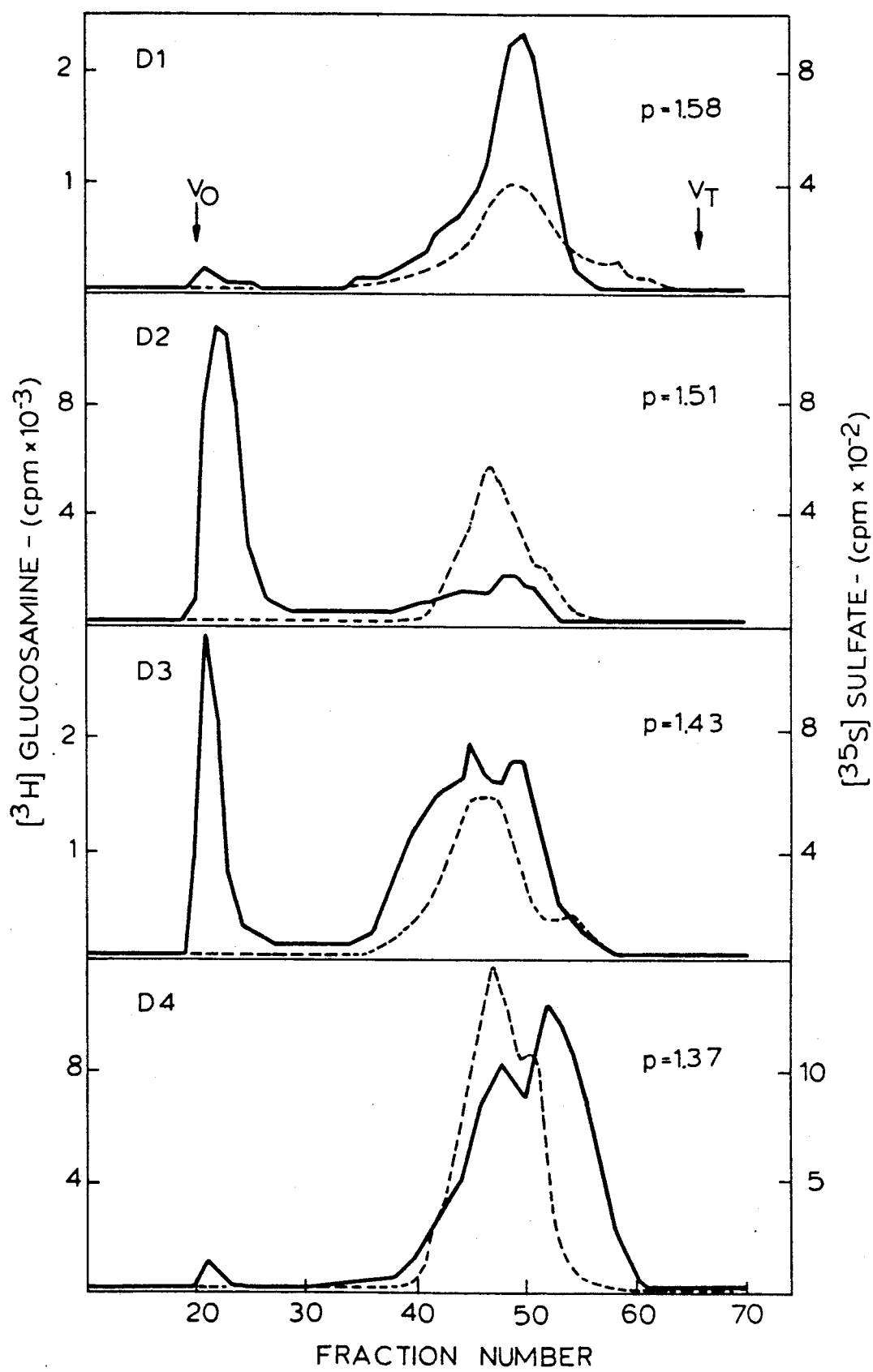

FIG. 2 illustrates the Sepharose CL-2B elution profile of radioactively labeled macromolecules synthesized by MTLn3 cells following dissociative CsCl-density-gradient ultracentrifugation. Cells that were labeled with [$^3$H] galactose, [$^3$H] glucosamine, or [$^3$H] serine yielded elution profiles containing two radioactive peaks ($K_{av}$=0.22 and 0.60). The first eluting peak contained 18.6% of [$^3$H] glucosamine, 0.45% of [$^3$H] galactose, and 0.1% of [$^3$H] serine incorporated into macromolecular material. The MTLn3 cells metabolically labeled with [$^3$H] leucine, [$^3$H] mannose, or [$^3$H] fucose resulted in a similar profile of two peaks, but the void volume fractions contained less that 0.05 to 0.002% of incorporated radioactivity. Only one radioactive peak was observed if the cells were incubated with Na$_2$$^{35}$SO$_4$($K_{av}$=0.60). Analysis of the D2 peaks revealed that the void volume fractions contained the majority (>90%) of rgp580, as detected by $^{125}$I-labeled PNA binding after desialylation and SDS-PAGE.

Figure 3:
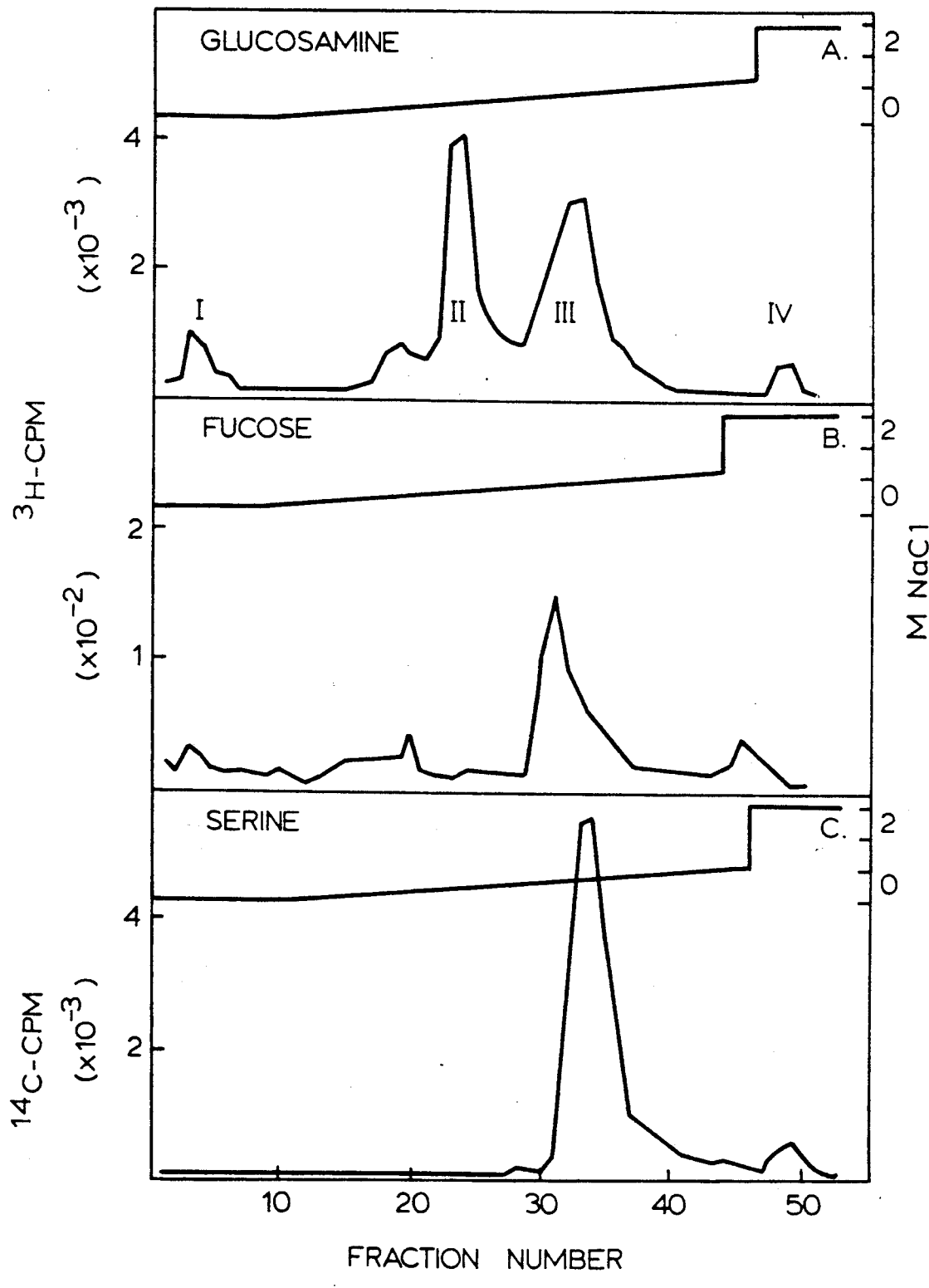
FIG. 3. Ion exchange chromatography on DEAE Sephacel columns of metabolically radiolabeled, pooled void volume fractions from the Sepharose CL-2B elution. Elution profiles of A,[$^3$H]glucosamine-, B,[$^3$H]fucose-, and C, [$^{14}$C]serine labeled samples from cultured MTLn3 cells are shown. The solid line represents the concentration of sodium chloride elution. The various fractions I, II, III, and IV were pooled for further analysis. The radioactive peaks were designated by their elution position as compared to the [$^3$H]glucosamine sample.

The Sepharose CL-2B void volume fractions from density fractions D1 to D3 which were pooled, desialylated, and then subjected to ion exchange chromatography on Sephacel DEAE-cellulose columns by using an NaCl elution gradient are shown in FIG. 3. Cells labeled with [$^3$H] glucosamine or [$^3$H] galactose resulted in column profiles containing four peaks (FIG. 3A, peaks I through IV). The radioactivity associated with peaks I through IV corresponded to 2.0%, 7.8%, 8.1%, and 0.9% of [$^3$H] glucosamine incorporated, respectively. In contrast, only three radioactive peaks were observed when MTLn3 cells were labeled with [$^3$H] mannose or [$^3$H] fucose (FIG. 3B; peaks I, III, and IV). Only the latter two peaks (III and IV) were found with [$^{14}$C] serine-labeled material (FIG. 3C).

e. Isolation of rgp580 from Solid Tumors

MTLn3 tumors used for the isolation of rgp580 were harvested, washed, and then homogenized in 5 volumes of extraction buffer per gram of wet weight tissue. The extracts were frozen at −80° C. or immediately used after filtration through Whatman 1 paper. The filtrate was then subjected to gel filtration on Sephadex G-50 columns (either 10×1 cm or 50×4 cm) equilibrated with extraction buffer minus the Zwittergent. The void volume fractions were pooled for further analysis.

The extracts were subjected to dissociative density gradient centrifugation as described above, and density fractions corresponding to p=1.48±0.07 g/ml were pooled. Appropriate portions were applied to a calibrated Sepharose CL-2B column, and the void volume fractions were pooled. As previously determined for the in vitro grown MTLn3 cells, the majority of a high molecular weight glycoprotein that bound $^{125}$I-labeled PNA after desialylation, and had a low migration in 7.5% SDS-PAGE gels, was found in the Sepharose CL-2B void volume fractions of the density gradient fraction D2 preparations. Aliquots of the pooled, dialyzed, and lyophilized void volume fractions were labeled with $^{25}$I by using the chloramine-T method as described by Hunter and Greenwood (1962), *Nature*, 194: 495–496, for proteinaceous material or periodate-[$^3$H] borohydride for sialic acid moieties as described by Mashborn et al (1974), *Biochem. Biophys. Acta*, 362: 366–374. Portions of the unlabeled and labeled extracts were combined and then applied to a DEAE Sephacel column. The $^3$H-labeled material eluted in four radioactive peaks similar to the [$^3$H] glucosamine labeled extract, except that the second peak contained less radioactivity. The $^{125}$I-labeled extract eluted with a profile most similar to the [$^3$H] serine-labeled material (cf. FIGS. 2 and 3A).

f. SDS-PAGE Characterization of rgp580

SDS-PAGE was performed according to the method of Laemmli (1973), *Nature*, 227: 680–685, by using a 7.5% acrylamide running gel and a 3% acrylamide stacking gel. For glycoprotein detection the gels were subjected with $^{125}$I-labeled PNA as described by Burridge (1976), *Proc. Natl. Acad. Sci.*, 77: 4457–4461, and then overlaid to mild acid treatment to remove sialic acid residues as described in Steck et al. (1983) *Exp. Cell Res.*, 147: 255–267. Alternatively, SDS-PAGE was performed by using the same system, except that a 2.0 to 17.5% linear acrylamide gradient gel using DATD (diallytartardiamide) instead of BIS (bisacrylamide) as the cross-linking agent and a stacking gel of 2% DATD acrylamide was used. The gel was constructed from a 37.8% acrylamide, 1.6% DATD stock solution, which increased the porosity of the gel and permitted migration of the rgp580 into the running gel matrix. Gels containing $^{125}$I-labeled material were washed, dried, and subjected to autoradiography that used Kodak X-Omat AR film with intensifying screens. For gels containing $^3$H-labeled or $^{14}$C-labeled samples, the destained gels were processed for fluorography by treatment with Enhance (New England, Nuclear Boston, Mass.), followed by drying and exposure of X-ray film to the gel. Densitometric scans of the exposed X-ray film were performed by using a Beckman DU-8 spectrophotometer with gel scan accessory. Isoelectric focusing in a sucrose density gradient was performed as described by Behnta et al. (1975), *Anal. Biochem.*, 69 1-9, except an equal mixture (V/V) of ampholines (pH 2.5 to 5.0 and 3.0 to 10.0, Pharmacia, Uppsala, Sweden) were used.

Figure 4A:
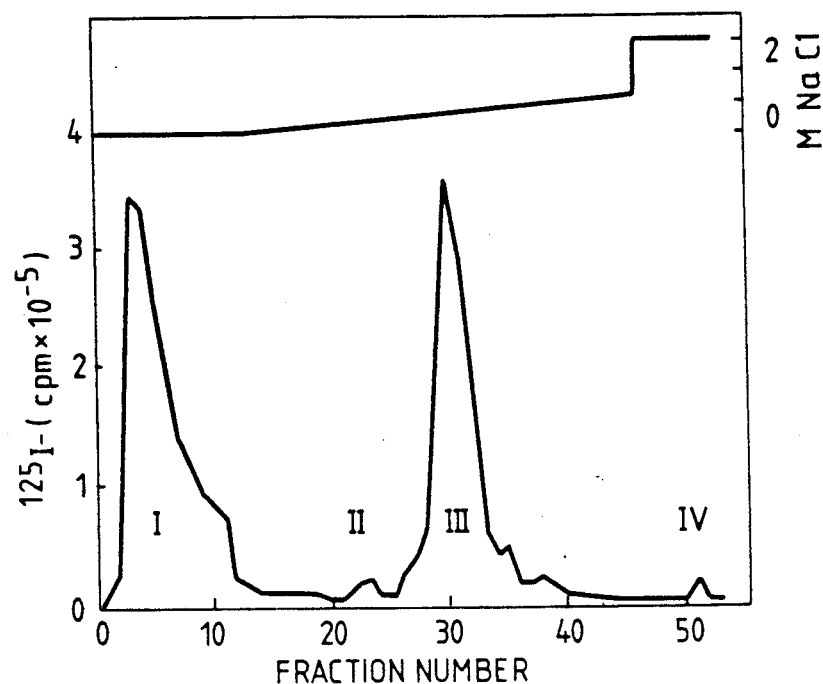
FIG. 4. Diethylaminoethyl (DEAE) Sephacel elution profile of rat tumor extract density gradient fractions (A). The solid line represents the concentration of sodium chloride used in the elution. The various peaks (I-IV) were pooled individually, and then aliquots were subjected to SDS-PAGE. Panel B, Autoradiogram of binding $^{125}$I-labeled peanut agglutinin (PNA) to the purified DEAE pooled peaks after SDS-PAGE on a 7.5% acrylamide gel. The lanes A-D correspond to peaks I-IV from the DEAE column. The binding of PNA was shown to be specific by control gel where lactose was included in incubation. The protein standards include myosin, B-galactosidase, phosphorylase, bovine serum albumin, and ovalbumin with $M_r(\times 10^3)$ of 200, 130, 92, 68 and respectively.

Aliquots of the different elution peaks from DEAE Sephacel were applied to 7.5% or 5% polyacrylamide gels, desialylated, and stained with $^{125}$I-labeled PNA. Only peaks III and IV bound $^{125}$I-labeled PNA (FIG. 4B, lanes C and D). Because rgp580 barely enters a 5% polyacrylamide gel, electrophoresis was conducted on gradient gels using DATD as the cross-linking reagent instead of BIS acrylamide. The use of a 2.0 to 17.5% DATD acrylamide gradient made possible the entry of the labeled materials into the gel. Examination of the four [$^3$H] glucosamine-labeled peaks from DEAE Sephacel chromatography after electrophoresis and fluorography showed that peak I contained only low molecular weight material. Peaks II to IV were observed to contain only high molecular weight material that migrated as diffuse but homogeneous bands (molecular weights of approximately 350,000 to 800,000 (FIG. 6A)). No other low molecular weight bands were detected in either metabolically or chemically-labeled fractions, even with over exposure of the X-ray films, suggesting that essentially all of the components were detected with these techniques.

When the [$^3$H] serine or $^{125}$I-labeled peaks were analyzed, similar results were obtained, except that peak II material was unlabeled. Estimation of average molecular weight of rgp580 by densitometric analysis of the fluorogram and comparison to standard proteins yielded an approximate value of 550,000 (FIG. 6B). The purification of rgp580 could be demonstrated by SDS-PAGE by using [$^{14}$C] serine-labeled cellular lysates of MTLn3 cells as the starting material. After purification, rgp580 was found to be homogeneous by SDS-PAGE analysis and to contain approximately 0.08% of the total [$^{14}$C] serine incorporated into acid-precipitable radioactivity.

To determine the composition of the various DEAE Sephacel peaks, aliquots were incubated with various degradative enzymes, and they were subsequently analyzed by SDS-PAGE. We found that the [$^3$H] glucosamine-labeled material in peak II appeared to be insensitive to pronase and to trypsin, but it could be degraded by Streptomyces hyaluronidase (Table I), suggesting that this component is hyaluronic acid. Components from Peaks III and IV had identical sensitivities to various enzymes and were degraded only by pronase (Table I). Furthermore, materials in peaks III and IV bound $^{125}$I-labeled PNA to high molecular weight components after mild acid treatment, suggesting that these peaks contained rgp580. Analysis of DEAE Sephacel fractions from chemically labeled MTLn3 tumor tissue showed identical characteristics.

TABLE I

| Analysis of DEAE Sephacel fractions by SDS-PAGE | | | | |
|---|---|---|---|---|
| Treatment[a] | Peak I | Peak II | Peak III | Peak IV |
| Molecular Weight | <10,000 | >350,000 | >350,000 | >350,000 |
| PNA binding | − | − | + | + |
| Sensitivity to: | | | | |
| Trypsin | − | − | − | − |
| Pronase | − | − | + | + |

TABLE I-continued

| Analysis of DEAE Sephacel fractions by SDS-PAGE | | | | |
|---|---|---|---|---|
| Treatment[a] | Peak I | Peak II | Peak III | Peak IV |
| Hyaluronidase | − | + | − | − |

[a]The molecular weight is the relative migration of [$^3$H] glucosamine or periodate-[$^3$H] borohydrate-labeled fractions on gradient DATD cross-linked polyacrylamide gels in SDS.

g. Chemical Characterization of rgp580

Enzymatic Treatments—The sensitivity of rgp580 to various degradative enzymes was determined by incubation of 1 hour at 37° C. with [$^3$H] glucosamine-, [$^3$H] serine-, or chemically labeled rgp580 in 100 ml of Dulbecco's PBS containing purified trypsin, pronase, papain, alphachymotrypsin, Subtilopeptidase A (1 or 10 mg/ml), collagenase type VI (1000 units/ml), chondroitinase ABC (1 unit/ml), Streptomyces hyaluronidase (100 turbidity-reducing units per milliliter), *Vibrio cholerae* neuraminidase (100 m units/ml), or β-galactosidase (1000 units/ml). The samples and untreated control were analyzed by SDS-PAGE on a 2.0 to 17.5% DATD acrylamide gradient gel, followed by densitometric quantitation of the exposed fluorogram.

Core Protein Determination—Unlabeled rgp580 or rgp580 metabolically labeled with [$^{14}$C] serine was added to 100 mg of bovine serum albumin used as carrier protein; the mixture was treated with trifluoromethylsulfonic acid in anisole (2:1 w/w) in a nitrogen-purged Reacti-vial for 10 or 30 min at 4° C. as described by Edge et al. (1981), *Anal. Biochem.*, 118: 131-137. The samples were extracted with diethyl ether, dialyzed, and lyophilized. The unlabeled, treated material was chemically labeled with $^{125}$I by using the chloramine-T method. Samples were analyzed on SDS-PAGE by using 2.0 to 17.5% DATD acrylamide gels.

Amino Acid Analysis—Samples of rgp580 were lyophilized in acid-washed tubes and hydrolyzed with 6N or 4N HCl for 4, 10, or 24 hours at 110° C. Analysis was performed using an LKB model 401 amino acid analyzer with norleucine as an added internal standard.

Alkaline Borohydride Treatment—Lyophilized samples of isolated rgp580 with radioactively labeled carbohydrate were treated with 50 mM NaOH, 1.0M NaBH$_4$ at 45° C. for 24 hours. The samples were neutralized with acetic acid, passed through a Dowex 50 (H+) column, and eluted with distilled water, and the fractions were dried repeatedly in the presence of methanol. The oligosaccharitol samples were redissolved in 5 mM Tris-HCl (pH 7.5) and applied to a QAE Sephadex (5×1 cm) column in the same buffer. The column was washed with 25 ml of 5 mM Tris-HCl, followed by a linear gradient elution to 120 ml of 0.2M Tris-HCl (pH 7.5). The radioactive peaks were pooled and then applied to a BioGel P6 column as described by Carlson (1968), *J. Biol. Chem.*, 243: 616-622.

Chemical Composition of rgp580—The amino acid composition of purified rgp580 is shown in Table II. As those of skill in the art will recognize, those values displayed in Table II which were obtained for gp580 isolated from cultured MTLn3 cells and an MTLn3 tumor are within experimental error. An experimental error of approximately ±10% is to be expected of such amino acid analyses. The values displayed in Table II are averages of four separate experiments. Glutamate, aspartate, and serine were the major amino acids present, with threonine, glycine, and lysine also represented in considerable quantities. These amino acids constituted more than half of the total composition of rgp580. The amino sugars, glucosamine and galactosamine, constituted about 20% of the composition of rgp580 (Table II).

TABLE II

Amino acid analysis of rgp580 synthesized by rat mammary adenocarcinoma cells

| Amino acid | Cultured MTLn3 cells residues/1000 amino acids | MTLn3 tumor |
|---|---|---|
| Aspartic acid | 105 | 103 |
| Threonine | 92 | 95 |
| Serine | 143 | 148 |
| Glutamic acid | 139 | 137 |
| Proline | 29 | 33 |
| Glycine | 101 | 98 |
| Alanine | 33 | 31 |
| Cysteine | 5 | 6 |
| Valine | 65 | 59 |
| Methionine | 7 | 8 |
| Leucine | 62 | 60 |
| Isoleucine | 37 | 38 |
| Tyrosine | 26 | 24 |
| Phenylalanine | 37 | 35 |
| Histidine | 13 | 16 |
| Lysine | 84 | 82 |
| Arginine | 22 | 25 |
| Glucosamine | 114 | 125 |
| Galactosamine | 90 | 102 |

Values represent averages of duplicate analyses for rgp580 purified from cultured MTLn3 cells and tumor tissues. The carbohydrate values were determined by extrapolation of the values at different hydrolysis times to zero time of hydrolysis. Tryptophan was not detected.

The rgp580 was deglycosylated with trifluoromethylsulfonic acid to produce the protein core. [$^{14}$C] serine-labeled rgp580 was treated with acid and then analyzed by SDS-PAGE. The protein core migrated as a single band with an estimated molecular weight of 150,000 kilodaltons. No other labeled bands were detected. The protein core of rgp580 isolated from tumor tissue and subsequently radioactively labeled with $^{125}$I was of identical size by SDS-PAGE.

Aliquots of purified [$^{14}$C] serine-labeled rgp580 were subjected to isopycnic centrifugation to determine its apparent density. Centrifugation in the presence of 4M GdnHCl revealed a density of around 1.432 g/ml (>90% between 1.475 to 1.398 g/ml). However, in the presence of an associative concentration of GdnHCl (0.5M), the apparent density was 1.615 g/ml (>90% between 1.671 to 1.563 g/ml). This increase in apparent density under weaker denaturing conditions has also been observed for hyaluronic acid and other highly acidic molecules. The acidic nature of rgp580 was confirmed by its high composition of anionic amino acids and large quantities of sialic acid. An estimate of the content of sialic acid on rgp580 was obtained by treatment of [$^3$H] glucosamine-labeled rgp580 with mild acid (50 mM H$_2$SO$_4$, 1 hour, 80° C.), followed by chromatography on a BioGel P4 column. Approximately 25.5% of the radioactivity incorporated into rgp580 was released by this treatment, suggesting that sialic acid is a major component of rgp580. Furthermore, rgp580 migrated as a diffuse band on sucrose density gradient isoelectric focusing with an isoelectric point of 3.2±0.5, thus confirming its acidic composition.

Data suggested that rgp580 possessed sialomucin-like characteristics, and this finding was confirmed by incubation of [$^3$H] serine-labeled rgp580 with various degradative enzymes. Sensitivity was assessed by subjecting the treated rgp580 to SDS-PAGE and densitometric analysis of the resulting bands. Purified rgp580 was resistant to a variety of proteases, chondroitinase ABC, and hyaluronidase (Table III). Digestion was observed only with pronase, Subtilopeptidase A and a combination of neuraminidase and B-galactosidase. Similar results were obtained when $^{125}$I-labeled MTLn3 tumor rgp580 was subjected to the degradative enzymes. These data suggest that rgp580 is a sialomucin, and that therefore it should contain a variety of O-linked oligosaccharides.

TABLE III

Sensitivity of rgp580 to degradative enzymes

| Enzyme | mg/ml or units | $M_r^a$ ($\times 10^3$) | relative density (area)[b] |
|---|---|---|---|
| Control | — | >400 | 1 |
| Trypsin | 1 | >400 | 1 |
|  | 10 | >400 | 1 |
| Pronase | 1 | 30–200 | .35 |
|  | 10 | n.d.[c] | 0 |
| Subtilopeptidase A | 1 | 50–300 | .43 |
|  | 10 | n.d. | 0 |
| Papain | 1 | >400 | 1 |
|  | 10 | >400 | 1 |
| Pepsin | 1 | >400 | 1 |
|  | 10 | >400 | 1 |
| a-Chymotrypsinogen | 1 | >400 | 1 |
|  | 10 | >400 | 1 |
| Collagenase | 1 | >400 | 1 |
|  | 10 | >400 | 1 |
| Chondroitinase ABC | 1 | >400 | 1 |
| Hyaluronidase | 100 | >400 | 1 |
| Neuraminidase | 100 | >400 | 1 |
| B-Galactosidase | 100 | >400 | 1 |
| Neuraminidase + B-Galactosidase | 100 + 100 | >350 | .9 |

[a]Following enzyme incubation the various samples were subjected to PAGE on 2 to 17% DATD cross-linked gels and fluorography.
[b]The relative density was normalized to the area under the densitometric scans of the fluorograms from the SDS-PAGE gels by using the untreated lane as 1. Areas were derived on a Beckman DU-8 spectrophotometer by using the lowest valley program.
[c]not detected Borohydride Release of rgp580 Oligosaccharides—A number of oligosaccharides were released by alkaline borohydride treatment of rgp580 that was radioactively-labeled with [$^3$H] glucosamine, [$^3$H] galactose and [$^3$H] fucose. [$^3$H] glucosamine-labeled oligosaccharides were applied to a QAE Sephadex column and separated into neutral (pass through fractions representing 22.5% of total radioactivity) and acidic (retained fractions, 76.3% of the radioactivity) components. The acidic fractions were eluted under conditions where mono-and di-sialylated oligosaccharitols are obtained (10 to 40 mM Tris-HCl, pH 7.5). Further fractionation was performed by gel filtration chromatography on BioGel P6 columns. Several relatively large radioactive peaks were observed for the acid oligosaccharitols. The majority of the neutral oligosaccharides were found to be associated with one radioactive peak. Oligosaccharides released from rgp580 that had been isolated from tumor tissue and its sialic acid moieties chemically labeled showed a similar profile.

EXAMPLE II

Development and Characterization of a Monoclonal Antibody Prepared Against rgp580

A rat hybridoma has been generated that produces monoclonal antibody (GP21:56) with specificity for rgp580 antigen present in high amount on highly metastatic 13762NF rat mammary adenocarcinoma cells. The hybridoma was made by the fusion of rat Y3 Ag1.2.3 myeloma cells with spleen cells from a rat immunized i.d. with purified rgp580. The rgp 580 appeared to be of low immunogenicity in syngeneic F344 rats because a total of 27 fusions were required to produce one hybridoma with specificity for this glycoprotein. In an attempt to increase the frequency of hybridomas secreting antibodies with specificity for rgp580, a number of different immunization protocols were used, such as i.d. and i.p. routes of antigen administration, in vitro immunization, and the use of both spleen and lymph nodes as sources of B cell blasts.

Enzyme-linked immunoabsorbent assays (ELISA) and direct binding assays, demonstrated that hybridomas produced in accordance with the present invention generated monoclonal antibodies which specifically bound to cloned target cell lines of the 13762NF rat adenocarcinoma in relation to their spontaneous metastatic potentials. Three times the number of GP21:56 antibody molecules bound to highly metastatic MTLn3 cells than to low metastatic MTC cells but GP21:56 showed little or no reactivity with other cell lines of rodent or human origin. Direct antibody binding assays using purified rgp580 bound to microtiter plates and immunoblotting using lysates of various 13762NF cell subclones confirmed that GP21:56 bound specifically to rgp580.

Kinetic studies indicated that GP21:56 does not have a high affinity for rgp580 but it does show high avidity to this glycoprotein. Once bound to MTLn3 cells in vitro, GP21:56 molecules were removed with a half-life of 24 hours. Localization studies using frozen tissue sections of 13762NF tumors indicated that GP21:56 reacts with tumor cells grown in vivo, in an analogous manner to in vitro cultured cells. Greater than 50% of the highly metastatic MTLn3 tumor cells were positive using immunoperoxidase techniques, approximately 20% of the intermediate metastatic MTF7 and MTLn2 cells and <10% of low metastatic MTC and MTPa cells were positive for rgp580. The expression of rgp580 was heterogeneous among the cells and was associated mainly with the tumor cell surface.

a. Materials and Methods

The following materials and methods represent techniques which the present inventors have found suitable in the preparation of monoclonals directed against rgp580. Although the following embodiments, utilize rat spleen/rat myeloma hybrids for hybridoma production, the present inventors have determined that other hybridoma techniques, such as those which utilize mouse/mouse hybrids, work as well.

Animals. Inbred 8-week-old Fischer (F344/CDL) rats (RT1[1]) were supplied by the Charles River Breeding Laboratories. Animals were quarantined for 7 days before use and fed standard rodent chow and unchlorinated spring water ad libitum. They were maintained under guidelines set forth by The University of Texas System Cancer Center and the Institute of Laboratory Animal Resources, National Research Council.

Cells and Cell Lines. The rat myeloma Y3 Ag1.2.3 (RT1[v]) cell line was obtained from C. Milstein, MRC Laboratories, Cambridge, England and was maintained in spinner culture in antibiotic-free DMEM and 20 mM Hepes in high glucose plus 10% FBS (Hyclone, Logan, Utah).

Cloned sublines of the 13762NF rat mammary adenocarcinoma (MTLn3, MTLn2, MTF7, MTC) and uncloned parental lines MTLY (from a lymph node metastasis) and MTPa (from the original tumor) were obtained and grown as described in Neri et al. (1982), *J. Natl. Cancer Inst.*, 68: 507. All cell lines and clones were screened routinely and found to be free of Mycoplasma and rodent virus contamination. The cell lines MTLn3, MTF7, MTC, MTLY, and MTPa were used between in vitro passages 10–18 and MTLn2 cells at passages 38–40.

Additional cell lines were established from tumor explants or rat mammary adenocarcinomas R32-30Ac (RT1[1]) CSE and MNU-F344 (Mason Research Institute, Worcester, Mass.). Tumor pieces were implanted subcutaneously in the syngeneic host and passaged twice in vivo before removal of the tumors. Tumor explants were enzymatically treated for 1 hour at room temperature with 0.25% trypsin (GIBCO, Grand Island, N.Y.) and 1% collagenase (Sigma Chemical Co., St. Louis, Mo.) to establish cell lines. Short-term cultures of normal adult rat fibroblasts were established from the xiphisternae of 8-week-old F344 rats using the same enzymatic procedure. Fetal lung fibroblasts were isolated from 14 to 16-day-old F344 rat fetuses without enzymatic treatment. The lungs were minced and placed in culture to allow the outgrowth of fibroblasts. These cell lines were maintained at low passage (less than passage 7) in AMEM plus 10% FBS, and unless stated otherwise, they were routinely cultured on 100 mm tissue culture plates (Corning Glass, Corning, N.Y.).

Melanoma cell lines SK-MEL-19, SK-MEL-75, DX1 and HS929 were obtained from J. Fogh (Memorial Sloane-Kettering Cancer Center, New York, N.Y.). The cell lines MDA286 and MDA436 were from R. Cailleau (U.T. M.D. Anderson Hospital and Tumor Institute at Houston, Houston, Tex.). Mouse mammary tumor cells 66, 67, 168.1 and 4526 were obtained from G. Heppner (Michigan Cancer Foundation, Detroit, Mich.)

Immunization Protocols.

(i) In vivo: 8-week-old F344 rats were immunized i.d., with a 1:1 (v/v) emulsion containing the D2 fraction described above, and Freund's Complete Adjuvant. Each rat was given a total of 0.4 ml at 4 i.d. sites (0.1 ml/site). Immunizations were repeated biweekly by injection of 0.1 ml of antigen in Freund's Incomplete Adjuvant into any resulting granulomas. A final i.d. challenge was given 4–5 days before removal of the spleen or cervical lymph nodes for fusion. Alternatively, rats were immunized by i.p. injection of antigen following similar procedures.

(ii) In vitro: The method used was a modification of that originally described by Luben and Mohler (1980), *Mol. Immunol.*, 17:935. Thymocyte-conditioned medium was obtained by culturing 10-day-old rat thymocytes for 48 hours in DMEM plus 2% rabbit serum (Quadroma, Inc., Escondido, Calif.), at a concentration of $2 \times 10^6$ cells/ml. After centrifugation, the conditioned medium was stored at $-70°$ C. For immunization, a single cell suspension was prepared from the spleen of a naive F344 rat. The splenocytes were incubated for 5 days with 10 ml of thymocyte-conditioned medium and antigen in DMEM with 2% rabbit serum. After 5 days, the resulting blast cells were fused with Y3 Ag1.2.3 myeloma cells using standard procedures.

Hybridoma Production. Spleen or lymph node cells were prepared by passage through a fine gauge mesh into 5 ml of medium. The cells were washed twice in serum-free medium and cell viability was determined by trypan blue exclusion. Spleen cells ($2 \times 10^8$) were mixed with $10^8$ Y3 Ag 1.2.3 cells, and the cell mixture was pelleted by centrifugation at $500 \times g$ for 5 min. The pellet was gently resuspended by the addition of 2 ml of 50% polyethylene glycol 1450 (J.T. Baker Chemical Co., Phillipsburg, N.J.) in DMEM adjusted to pH 7.2, over 1 minute. The fusion mixture was rocked for another minute, diluted with 8 ml of DMEM, and centrifuged for 5 min at $500 \times g$. The cells were resuspended in 200 ml of DMEM containing 20% FBS, $10^{-4}M$ hypoxanthine (Sigma, St. Louis, Mo.), $4 \times 10^{-7}M$ aminopterin (Sigma) and $1.6 \times 10^{-5}M$ thymidine (HAT medium), (Sigma). Aliquots (1 ml) were distributed into Costar 24-well plates (Costar, Cambridge, Mass), which had been seeded 24 hours previously with $2 \times 10^4$ radiated (30 Gy, gamma irradiation) rat fibroblasts/well. After 24-hr incubation at 37° C. under standard culture conditions, HAT medium (1 ml) was added. The cell fusions were incubated for 7-14 days before screening for the presence of hybrids.

Screening for Specific Antibody. Hybridoma cultures were tested for the production of specific antibody using an ELISA. Monolayers of target cells were grown to confluency in 96-well microtest plates, fixed with 0.5% glutaraldehyde, and stored at −20° C. in PBS containing 1.0% bovine serum albumin (BSA). Samples of hybridoma culture supernatants (50 ul/well) were incubated with the target cells for 1 hour at room temperature. The target cells were washed three times with PBS plus 0.05% BSA. Biotinylated goat/rat IgG (Vector Labs., Burlingame, Calif.) diluted 1/1000 in PBS containing 1% BSA was added (50 ul/well), and has incubated with the cells for 1 hour at room temperature. The cells were washed three times followed by the addition of streptavidin-bridging reagent (Bethesda Research Laboratories, Inc. Gaithersburg, Md.) (50 ul/well) diluted 1/1000 in PBS plus 1% BSA, and incubation occurred for an additional 45 min at room temperature.

The plates were washed six times with PBS plus 0.05% BSA. Bound antibody was quantitated using o-phenylenediamine (1 mg/ml) reagent (100 ul well), which was dissolved in 0.1M citrate buffer, pH 4.5 and 0.012% hydrogen peroxide. After 15 minute incubation in the dark, absorbance at 450 nm was determined using a Titertek Multiscanner (Flow Laboratories, McLean, Va.). In all assays, a Y3 Ag1.2.3 culture supernatant was used as the negative control. Supernatants were considered positive for gp580 specific monoclonal antibody (MAb) if they possessed absorbance equal to or greater than two standard deviations above background. Hybridomas from positive wells were cloned twice by limiting dilution using irradiated rat fibroblasts as feeder cells.

Other MAb binding assays used $^{125}I$-labeled, affinity-purified antibodies to rat F(ab')$_2$, (Dr. C. J. Dean, Chester Beatty Research Institute, Sutton, Surrey, England). Samples from culture supernatants or purified MAb were incubated for 1 hour at 4° C. with confluent monolayers of viable cells or at room temperature with fixed cells grown in 96-well microtest plates. Bound MAb was determined by incubation with $5 \times 10^5$ cpm/well of $^{125}I$-labeled sheep/rat F(ab')$_2$ for 1 hour at 4° C. (viable cells) or at room temperature (fixed cells). The cells were washed with PBS and lysed with 200 μl of 2N NaOH. Radioactivity was determined by counting in a Beckman Model 8000 gamma counter.

Rates of MAb Clearance by MTLn3 cells In Vitro. Exponentially growing clones of MTLn3 cells in 96 well-plates were washed once in AMEM containing 5% FBS and incubated on ice for 1 hr with 50 μl/well of culture supernatant (10 μg/ml antibody). The plates were washed three times with AMEM, and each plate was divided into four sections. To determine the quantity of MAb bound initially one section was incubated with 30 μl of $^{125}I$-labeled sheep/rat F(ab')$_2$ for 1 hour at 4° C. The remaining sections were incubated at 37° C. in an atmosphere of 95% air and 5% $CO_2$ for 0 to 32 hours. At regular intervals, one section was processed as described above. After thorough washing, the cells were lysed and the radioactivity determined as described above.

Plates for Binding of MAb GP21:56 to rgp580. Purified rgp580 was immobilized overnight on Immunotech I plates (A/S Nunc, Kamstrap, Denmark) by the following method. A solution of rgp580 (1 μg/ml) was first sonicated and aliquots were pipetted (50 ul/well) into microtest plates. The plates were washed three times with PBS and then incubated with PBS plus 1% BSA for 1 hour at room temperature. The plates were stored at −20° C. in PBS plus 1% BSA.

Kinetic Studies. Cloned MTLn3 cells were washed once with PBS plus 1% BSA and incubated with $^{125}I$-labeled GP21:56 (1 Ci/mg) at 4° C. For the determination of saturation binding, MTLn3 cells ($8 \times 10^4$) were incubated with $^{125}I$-labeled GP21:56 ($4.2 \times 10^4$ CPM), and aliquots were taken at regular intervals up to 1½ hours. The aliquots were washed three times with PBS/BSA buffer, and radioactivity determined as described above. Nonspecific binding was estimated by measuring the radioactivity bound when the samples were incubated in the presence of 1000 times excess of unlabeled antibody. The rate of dissociation was determined by incubating MTLn3 cells for 1 hour with $^{125}I$-labeled GP21:56 as above; 1000-times excess of cold antibody was then added, and aliquots removed over a period of 1½ hours. The cells were washed three times with PBS/BSA buffer, and the cell-associated radioactivity was determined by the standard procedure.

Purification of MAb. MAbs were isolated from culture supernatants by affinity chromatography after concentration by ammonium sulfate (40% saturation) precipitation. The immunosorbent column was made by linking an anti-rat K chain MAb, (Mark 1; H. Bazin, Brussels, Belgium) to Affi-Gel 10 (10 mg protein/ml beads). Elution of MAb GP21:56 from the immunosorbent column was accomplished with 3M potassium thiocyanate, and fractions (1 ml) were collected and immediately neutralized with 0.1 Hepes buffer, pH 8.0. Protein concentrations were determined using the Bradford assay as described in Bradford (1976), *Anal. Biochem.*, 72: 248, and the purity of the MAb was assayed by polyacrylamide gel electrophoresis in sodium dodecyl sulfate (SDS-PAGE). Antibody isotype was identified by double diffusion analysis in soft agar using antisera to rat $IgG_1$, $IgG_{2a}$, $IgG_{2b}$, $IgG_{2c}$ and IgM (Miles Laboratories, Inc., Naperville, Ill.). Purified antibodies were labeled with $^{125}I$ (ICN Pharmaceuticals, Irvine, Calif.) to a specific activity of 2 Ci/mg by the chloramine-T method.

Immunoperoxidase Procedures. Tissue samples of 13762NF adenocarcinoma subclones were obtained from tumors grown subcutaneously (s.c.) in the mammary fat pads of F344 rats 23 days after the injection of $10^6$ tumor cells/rat. The tissues were snap frozen in liquid nitrogen and stored at $-20°$ C. until required. Cryostat sections (4 um thick) were used for immunoperoxidase staining. The procedure used the Vectastain ABC anti-rat IgG kit (Vector Laboratories, San Francisco, Calif.) with Diaminobenzidine (DAB) (1 mg/ml in Tris-HCl, pH 7.2) as a substrate. Sections were counter-stained with Meyer's hematoxylin and examined in a Leitz photomicroscope.

Immunoblotting. Western blots were performed essentially as described by Towbin et al. (1979), *P.N.A.S.*, 76: 4350. Proteins were electrophoretically transferred overnight from 2-17.5% DATD cross-linked, denaturing polyacrylamide gradient gels to nitrocellulose paper at 50 volts and 0.29 amps. Antigen was detected by incubating the blot with $^{125}$I-labeled antibody for 3 hours and then performing autoradiography using Kodak X-OMAT AR film.

b. Generation and Specificity of MAb GP21:56

A number of different in vivo and in vitro immunization procedures were employed in order to produce MAbs against rgp580 (See Table IV). Naive rats were challenged either intradermally (i.d.) or intraperitoneally (i.p.) with rgp580, and both the spleen and cervical lymph nodes were used as a source of B blast cells for fusion with the Y3 Ag1.2.3 myeloma cells. Additionally, in vitro immunization procedures were used to increase the probability of producinq hybridomas with the desired specificity. From a total of 27 fusions using these immunization techniques yielded only one MAb (designated GP21:56) which showed specific ELISA reactivity with MTLn3 cells in the primary screening assay. The frequency of hybrids formed per fusion was low. On the average, only 20-25% of the wells were positive for growth, although this was somewhat dependent on the immunization protocol and source of B blast cells. In some fusions, few or no hybrids were detectable.

The frequency of hybrids formed with specificity against rgp580 was significantly lower as compared to that of other antigens. As a control, spleen from a naive rat was used and found that the number of wells with hybridoma growth was usually in the order of 16-20%, but antigens other than rgp580 yielded up to 100% of the wells positive for hybrid growth. The low frequency of hybrids formed against rgp580 suggests that this antigen is of low immunogenicity in the syngeneic host. Because of limiting quantities of rgp580, hybrids were originally selected on the basis of their reactivity with MTLn3 cells. Under these conditions only MAb GP21:56 was reactive.

Binding of MAb GP21:56 to Purified rgp580. The ELISA, described in the previous section, suggested that MAb GP21:56 recognizes an epitope present on rgp580. To confirm this, the ability of MAb GP21:56 to recognize purified rgp580 was determined in a solid-phase antibody binding assay using immobilized rgp580 as an antigen. Binding of affinity-purified MAb GP21:56 (100 ug/ml) was determined in triplicate samples. The MAb GP21:56 bound specifically to rgp580, while MAbs with specificity for other cell surface antigens expressed on the 13762NF adenocarcinoma did not bind to rgp580.

Figure 5:
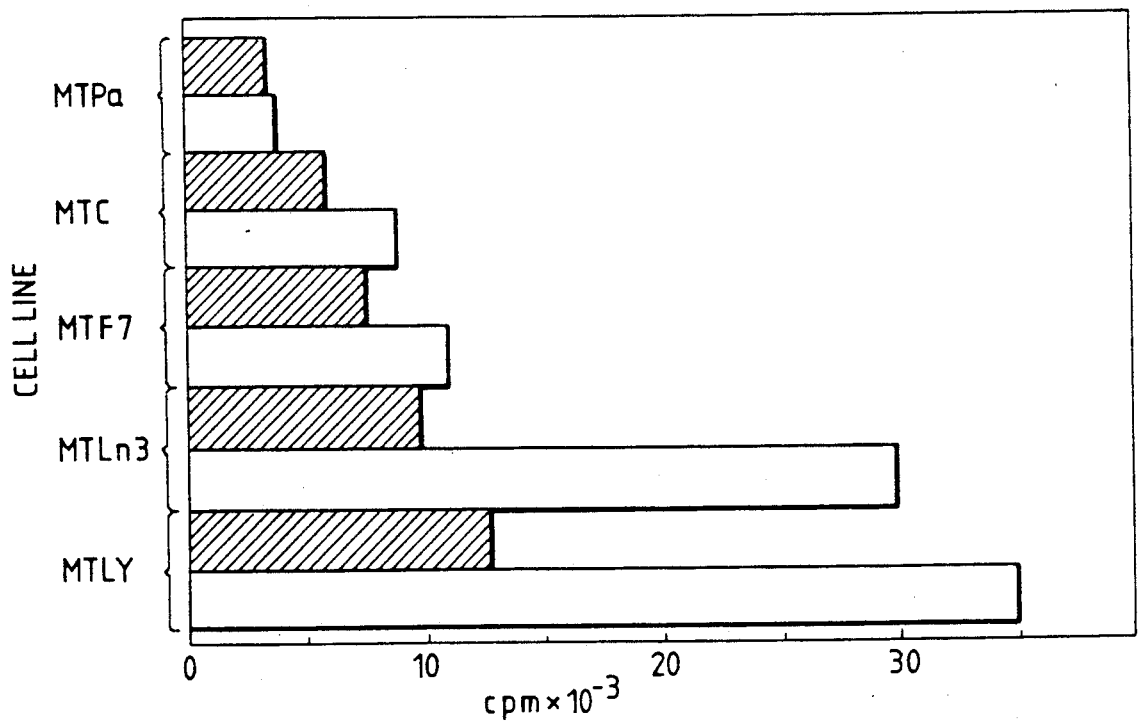
FIG. 5. Binding of MAb GP21:56 to glutaraldehyde-fixed and unfixed, viable 13762NF adenocarcinoma cells. $^{125}$I-labeled MAb GP21:56 was incubated for 1 hr, and the cell bound reactivity determined directly after lysis of the cells. Fixed cells (solid bars); unfixed cells (open bars).

Binding of MAb GP21:56 to Uncloned and Cloned 13762NF Cell Lines. The previous assay showed that MAb GP21:56 reacted with purified rgp580. Using various sublines of the 13762NF mammary adenocarcinoma, quantitative data on the reactivity of MAb GP21:56 with these cloned cell lines was obtained. A direct binding assay to glutaraldehyde-fixed MTLn3, MTF7, MTC, and MTPa cells were used, and bound MAb was detected using $^{125}$I-labeled sheep/rat $F(ab')_2$. It can be seen from FIG. 5 that at high MAb concentrations, the binding profile of Mab GP21:56 to the 13762NF cells is related to the metastatic potential and the cellular quantities of rgp580 of these cell clones. The results indicated that there was three times the amount of MAb GP21:56 bound to MTLn3 than to MTF7 or MTC cells, and there was little binding to parental MTPa cells. An alternative explanation for these results is that there was reduced availability of the rgp580 epitope for binding GP21:56 as a consequence of the fixation process, or that the expression of additional "masking" proteoglycans on the cell surface prevented binding of the MAb. However, NP40 extracts of unfixed 13762NF reacted with GP21:56 similar to intact cells and the chemical amounts of rgp580 extracted from various 13762NF cell clones agreed with MAb binding data.

In addition, the binding of MAb GP21:56 was the same on viable, unfixed cells and fixed cells. Using the cell lines described above, plus the parental line MTLy

TABLE IV

| | Production of Monoclonal Antibodies to gp580 | | | | |
|---|---|---|---|---|---|
| Immunogen | Immunization Protocol | Source of B Cells | No. of Fusions | Total No. Wells with Hybrids/ Total No. Wells (%) | No. Ab Reactive Clones |
| gp580[a] | i.d. | spleen | 8 | 169/768 (22.0) | 1 |
| gp580[a] | i.d. | l. node | 2 | 12/192 (6.3) | 0 |
| gp580[a] | i.p. | spleen | 5 | 71/480 (14.8) | 0 |
| gp580[b] | | spleen | 8 | 286/768 (37.2) | 0 |
| gp580[c] | | spleen | 4 | 0/384 (0.0) | 0 |
| MTln3 cells[d] | s.c. | spleen | 8 | 653/768 (85.0) | 73 |
| None[e] | NA | spleen | 2 | 12/72 (16.6) | 0 |

Abbreviations:
NA: not applicable
[a]Animals challenged biweekly with gp580, primed with antigen emulsified in Complete Freund's Adjuvant, and rechallenged with antigen emulsified in Incomplete Freund's Adjuvant (1:1).
[b]In vitro immunizations where the spleen was removed from a naive animal and stimulated in vitro with gp580.
[c]In vitro immunizations where the animal was challenged once in vivo, and then the spleen was removed and challenged in vitro.
[d]MTln3 cells injected s.c. and the spleen removed after 21 days tumor growth.
[e]Spleen taken from a naive rat.

(an uncloned cell line established from a lymph node metastasis) was also tested. MTLy is highly metastatic. MAb GP21:56 had essentially the same pattern of reactivity to various fixed and viable 13762NF cell clones, although the actual binding of MAb GP21:56 to viable cells was approximately 40% lower than to fixed MTLn3 or MTLy cells.

Identification of the MAb GP21:56 Antigen. Evidence confirming the specificity of GP21:56 for rgp580 was demonstrated by immunoblotting of $^{125}$I-labeled, affinity-purified GP21:56 to SDS polyacrylamide gels containing cell lysates of the 13762NF clones and purified rgp580. In these experiments, GP21:56 bound to the high molecular weight component identified as rgp580.

Specificity of MAb GP21:56 Binding to In Vitro Grown Cell Lines. To establish the specificity of MAb GP21:56, the binding of this MAb was tested against a number of established cell lines using an ELISA. Cell lines of rat, mouse, and human origin were used, and the results showed that GP21:56 had specificity for the cloned cell lines of the 13762NF rat mammary adenocarcinoma. Very little reactivity was noted on other cultured rat tumor cells or normal fibroblasts, and there was negligible binding of GP21:56 to established mouse or human mammary tumor cells or to human melanoma cell lines. However, very good reactivity has been noted between GP21:56 and human tumor biopsy sections, particularly with those human tumors of mammary origin. In addition, cross-reactivity was not observed with fetal rat lung or liver fibroblasts.

Saturation Binding of MAb GP21:56 to MTLn3 Cells. The affinity of GP21:56 for the rgp580 antigen expressed on MTLn3 cells was determined by measuring the association and dissociation kinetics of binding of $^{125}$I-labeled GP21:56. MAb GP21:56 had a relatively slow rate of association with MTLn3 cells; approximately 1 hour was required for saturation binding. The initial rate of dissociation for GP21:56 bound to MTLn3 cells was slow, with very little release during the 1½ hour assay. These data indicate that GP21:56 does not have a high affinity for the cellular antigen, but once bound it does have a high avidity.

Modulation of Cell-Bound MAb GP21:56. The rate of clearance of MAb GP21:56 from the surface of cultured MTLn3 cells was determined by following the fate of surface-bound MAb. Culture supernatant (10 ug/ml MAb) was incubated with MTLn3 cells for 1 hour, and the MAb remaining on the cell surface was then quantitated with $^{125}$I-labeled sheep/rat F(ab')$_2$ at various times, up to 32 hours. The half-life of surface-bound GP21:56 on MTLn3 cells in vitro was estimated to be on the order of 24 hours.

Reactivity of MAb GP21:56 with 13762NF Tumor in Tissue Sections. To determine the distribution of rgp580 on tumors growing in situ and to confirm the reactivity of MAb GP21:56 tumor tissues from syngeneic F344 rats, the distribution of bound MAb was examined. Tumors formed from s.c. injection of $10^6$ MTLn3, MTF7, MTLn2, or MTPa cells were removed at 23 days and frozen. MAb reactivity was determined using immunoperoxidase staining procedures. MAb GP21:56 showed extensive but heterogeneous binding to MTLn3 cells. Not all MTLn3 cells were reactive, but in general, greater than 50% of the cells reacted with the MAb. Most of the reactivity was found to be associated with the cell surface and extra-cellular matrix. MTF7, MTLn2, and MTPa tumors had much lower percentages of GP21:56-reactive cells. Approximately 20% of the cells in MTF7 and MTLn2 tumors were reactive with GP21:56, while MTPa tumors had very few GP21:56 reactive cells. In all of the 13762NF sublines examined the localization of GP21:56 was heterogeneous and predominantly associated with the cell surface.

EXAMPLE III

Isolation and Characterization of hgp580

Utilizing techniques similar to those employed in the isolation of rgp580, a protein, designated hgp580, exhibiting similar characteristics to rgp580 has been identified and isolated from a human cell source. This glycoprotein is biochemically distinguishable from rgp580, however, it has been determined that hgp580 is a tumor-associated "marker" and is similarly functional in the development of human tumor immunodiagnostic reagents. It has been determined that antigenic preparation made against hgp580 are generally preferrable to those prepared against rgp580 in human tumor immunodiagnosis. Those of skill in the art will recognize that slight variations between techniques utilized for hgp580 and those described for rgp580 generally represent non crucial variations, unless otherwise indicated.

a. Isolation of hgp580

Tissues and Cells. The rat 13762NF cell lines and clones were grown in AMEM with 10% fetal bovine serum, no antibiotics, in a humidifed atmosphere at 37° C. as described in Example I. Human breast carcinoma tumors were obtained from the Department of Pathology, M.D. Anderson Hospital and Tumor Institute after surgical removal or autopsy.

Isolation of hgp580. One method which has been employed for the purification of hgp580 basically follows the method described for the isolation of rgp580. Briefly, tumors were minced and extracted with (5 volumes per g of tissue wet weight) 4M guanidine hydrochloride and 4% Zwittergent 3-12 in 0.1M sodium acetate pH 6.0 containing protease inhibitors (5 mM EDTA, 2 mM L-tosylamide 2-phenylethylchloromethylalkaline, 50 mM 6-aminohexanoic acid, 5 mM phenylmethylsulfonylfluoride, 5 mM benzamidine-HCl, and 10 units/ml aprotinin) for 12 hours at 4° C. The extracts were filtered through Whatman 1 paper and then subjected to gel filtration on a Sephadex G-50 column (50×4 cm) equilibrated with extraction buffer excluding the Zwittergent. The void volume fractions were pooled, and cesium chloride added (0.55 g CsCl/g of solution). The samples were centrifuged 48-60 hours at 35,000 rpm in a Beckman TI 50.2 rotor at 9° C. The gradients were then fractionated into eight equal fractions and their density determined. Fractions with a density between 1.55-1.45 g/ml were pooled and applied to a calibrated Sepharose CL-2B column (100×2 cm) equilibrated with 4M guanidine hydrochloride in 0.1M sodium acetate, pH 5.8. The void volume fractions were then pooled, dialyzed, and lyophilized. Aliquots of the fractions were then chemically labeled with $^{125}$I and chloramine T for protein or periodate-[$^3$H] borohydride for sialic acid.

Further purification was achieved by ion exchange chromatography on a Sephacel DEAE column (5×1 cm) equilibrated with 8M urea, 0.2% Triton X-100 and 50 mM Tris HCl, pH 6.8. Elution was performed with a sodium chloride gradient (0 to 1M) followed by a high salt wash (3M). The appropriate fractions, as determined by radioactive profiles, were then pooled, dialyzed and lyophilized Improved Method for Isolation of hgp580—In an improved method for isolation of hgp580, the tumor tissue was washed in PBS and then minced and extracted in a solution of 4M guanidine HCl, 1% Zwittergent 3-12, 0.1M sodium acetate, pH 6.2, in the presence of protease inhibitors. After an overnight extraction of approximately 18 hours, the solution was filtered through a fine mesh nylon filter and then applied to a preparative Sephadex G-50 column (4×50 cm) equilibrated with 8M urea, 5 mM sodium chloride, and sodium acetate pH7.0. The void volume fractions were collected and then applied to a DEAE-Sephacel column in the same buffer, except containing 0.2% CHAPS. The column was washed with equilibration buffer and then eluted with an increasing linear sodium chloride gradient. The various peak fractions were pooled, diluted three times (v/v) with 8M urea and applied to a DEAE-Sephacel column (1 ml). The material was then eluted with a small volume of 4M guanidine HCl. The eluant was then subjected to gel filtration chromatography on a calibrated Sepharose CL-2B column (2×100 cm) in 4M guanidine HCl, 0.2% CHAPS, and 0.1M sodium acetate pH 5.8. The void volume fractions were pooled and represent purified hgp580 and are assayed for purity by SDS-polyacrylamide gel electrophoresis followed by silver staining.

b. Chemical Characterization of hgp580

Analysis of hgp580 by polyacrylamide gel electrophoresis in sodium dodecyl sulfate (SDS-PAGE) was performed by two methods. For glycoprotein detection, SDS-PAGE was performed using a 7% acrylamide running gel and a 3% acrylamide stacking gel. The gels were fixed, treated with 50 mM $H_2SO_4$ for 1 hour at 80° C. to desialylate the glycoprotein, and then were overlaid with $^{125}$I-labeled peanut agglutinin, washed and dried. In order to achieve migration of the glycoproteins into the polyacrylamide gel, a linear gradient gel was used with N,N-diallyltartardiamide (DATD) as the crosslinking agent rather than N,N-methylenebisacrylamide. The stacking gel was constructed of 2% DATD acrylamide. Gels containing $^{125}$I-labeled material were subjected to autoradiography using Kodak X-Omat AR film with intensifying screens. For gels containing $^3$H-labeled samples, the destained gels were treated with Enhance (New England Nuclear, Boston, Mass.) before drying and were then exposed to the X-ray film.

The effect of various degradative enzymes on rgp580 and hgp580 was determined by incubation of $^{125}$I-labeled glycoprotein in 100 ml of DPBS for 1 hour at 37° C. The enzymes assayed were trypsin, pepsin, pronase, papain (activated with 1 mM B-mercaptoethanol), a chymotrypsin, Subtilopeptidase A (at 1 and 10 mg/ml), Chondroitinase ABC (1 unit/ml), Streptomyces hyaluronidase (100 TRU/ml), *Vibrio chlorea* neuraminidase (100 m units/ml) and B-Galactosidase (10 units/ml). The samples and an untreated control were then subjected to SDS-PAGE analysis on a 2 to 17.5% DATD acrylamide gel, dried, and exposed to X-ray film. The resulting film was densitometrically scanned on a Beckman DU-8 using the gel scan accessory.

The sialic acid moieties were chemically labeled with periodate-[3H] borohydride and then the O-linked (linkage of carbohydrate to serine or threonine) oligosaccharides were released by treatment with 50 mM NaOH in 1M $NaBH_4$ at 45° C. for 24 hours under a $N_2$ atmosphere. The reaction was stopped by addition of acetic acid, and the sample was passed through a Dowex 50 (H+) column. The sialic acid containing oligosaccharides were analyzed in a Bio Gel P6 column equilibrated with 50 mM pyridinium acetate, pH 5.3.

Amino acid analysis of rgp580 and hgp580 was performed on a LKB model 401 amino acid analyzer with norleucine as an internal standard. Samples were lyophilized in acid washed tubes and then hydrolyzed with Gdn HCl for 24 hours at 100° C.

The results of the comparative characterization of the hgp580 are displayed in Table V. As depicted therein, hgp580 shares many biochemical attributes with rgp580. However, the two are distinguishable on the basis of amino acid analysis. The results of the amino acid analyses displayed in Table V represent the average of four experiments and are considered accurate within ±10%.

TABLE V
Properties of Purified Rat and Human Sialogalactoprotein gp580

| Property | Rat gp580 | Human gp580 |
|---|---|---|
| 1. Molecular weight | | |
| a. gel electrophoresis | 580,000 | 580,000 |
| b. gel chromatography | 550,000 | 550,000 |
| 2. Density | | |
| a. 4 M Guanidine-HCl | 1.4 g/ml | 1.4 g/ml |
| b. 0.5 M Guanidine-HCl | 1.6 g/ml | |
| 3. Binding of Peanut Agglutinin | | |
| a. untreated | − | − |
| b. desialylation | + | + |
| 4. Resistance to Degradative Enzyme | | |
| a. Trypsin | + | + |
| b. Papain | + | + |
| c. Pepsin | + | + |
| d. Chondroitinase ABC | + | + |
| e. Hyaluronidase | + | + |
| f. Pronase | − | − |
| g. Subtilopeptidase A | − | − |
| 5. Oligosaccharides | | |
| a. bind to lectins | + | + |
| b. released by NaOH/NaBH$_4$ | + | + |
| c. sialic acid | + | + |
| 6. Amino Acids and Amino sugars (Residue/1,000 amino acids) | | |
| a. Aspartic Acid | 103 | 120 |
| b. Threonine | 95 | 87 |
| c. Serine | 148 | 166 |
| d. Glutamic Acid | 137 | 154 |
| e. Proline | 33 | 37 |
| f. Glycine | 98 | 78 |
| g. Alanine | 31 | 26 |
| h. Cysteine | 6 | N.D. |
| i. Valine | 59 | 65 |
| j. Methionine | 8 | N.D. |
| k. Leucine | 60 | 56 |
| l. Isoleucine | 38 | 38 |
| m. Tyrosine | 24 | 23 |
| n. Phenylalanine | 35 | 29 |
| o. Histidine | 16 | 11 |
| p. Lysine | 82 | 94 |
| q. Arginine | 25 | 16 |
| r. Glucosamine | 125 | 147 |
| s. Galactosamine | 102 | 113 |

N.D. = not detected

EXAMPLE IV:

Development of Monclonal Antibodies to hgp580

Monoclonal antibodies exhibiting specificity for human tumor cells have been generated using an hgp580 antigen preparation in a very similar fashion as described above for the rgp580 antigen. In a preferred embodiment, described as follows, hybridomas were developed using spleen cells from rats immunized with a preparation which contains hgp580 and the spleen cells fused to a rat myeloma cell line. However, other cell systems, for example, mouse/mouse hybrids, may be successfully utilized for the production of hybridomas. Any variations between the following procedures for the generation of monoclonals against hgp580 and the procedures previously described for rgp580 are not crucial but rather represent refinements.

a. Materials and Methods

Animals. Inbred 8 week old Fischer (F344/CDL) rats (RTl[1]) were supplied by Harland Sprague Dawley, Houston, Tex. Rats were fed standard rodent chow and unchlorinated spring water ad libitum, and maintained under guidelines set forth by the University of Texas System Cancer Center and Institute of Laboratory Animal Resources, National Research Council.

Cells and Cell Lines. The rat myeloma Y3Ag1.2.3 (RTl[v]) was obtained from C. Milstein, MRC Laboratories, Cambridge, England, and was maintained in spinner culture in antibiotic free Dulbecco's Modified Eagles medium (DMEM) and 20 mM Hepes high glucose plus 10% fetal bovine serum (FBS), (Hyclone, Logan, Utah).

Cloned sublines of the 13762NF rat mammary adenocarcinoma (MTLn3, MTLn2, MTF7, MTC) and uncloned MTPa were obtained and grown as described above. All the cell lines were screened routinely and found to be free of mycoplasma and virus contamination.

Additional cell lines were established from rat mammary adenocarcinoma R32-30Ac (RTl[1]), DMBA-1 (RTl[1]), rat mammary adenocarcinoma MNU-F344- (RTl[1]) and the rat fibrosarcoma CSE (RTl[1]). Short term cultures of adult and fetal rat fibroblasts were obtained as described above. Human melanoma lines were supplied by J. Fogh (Sloane Kettering Cancer Center, New York, N.Y.), MDA-436 was obtained from R. Cailleau, and human mammary brain metastases from the Department of Neuro-oncology, M. D. Anderson Hospital, Houston, Tex.

Hybridoma Production. Hybridomas were generated using spleen cells from rats immunized i.d. with hgp580 following the protocol described above for rgp580. Spleen cells were prepared by passage through a fine gauge mesh into 5 mls of medium. The cells were washed twice in serum free medium, and viability determined by trypan blue exclusion. Spleen cells ($2 \times 10^8$) were mixed with $10^8$ Y3Ag1.2.3 rat myeloma cells, and the cell mixture was pelleted by centrifugation at $500 \times g$ for 5 minutes. The pellet was gently resuspended by addition of 2 mls 50% polyethylene glycol 1450 (J. T. Baker Chemical Co., Phillipsburg, N.J.) in DMEM, adjusted to pH 7.2, over a 1 minute period. The fusion mixture was rocked for a further minute, diluted with 8 ml DMEM and centrifuged for minutes at $500 \times g$. The cells were resuspended in 200 mls of DMEM containing 20% FBS $10^{-4}$ hypoxanthine (Sigma), $4 \times 10^{-7}$M aminopterin (Sigma) and $1.6 \times 10^{-5}$M thymidine (HA medium: Sigma). Aliquots (1 ml) were distributed into Costar 24-well plates (Costar, Cambridge, Mass.), which had been seeded 24 hours previously with $2 \times 10^4$ irradiated (30 Gy, gamma irradiation) rat fibroblasts/well. After 24 hours incubation at 37° C. in standard culture conditions, 1 ml of HAT medium was added. The fusions were incubated for 7–14 days under the above conditions before screening for the presence of hybrids.

Screening for Specific Antibody. Hybridomas were tested for the production of specific antibody using an ELISA assay as follows. To test for antibodies to hgp580, purified antigen was sonicated and then immobilized overnight on Immunotech-1 plates (50 μl/well; A/S Nunc, Kamstrap, Denmark). The plates were washed three times with Dulbecco's phosphate buffered saline (DPBS), and once for 1 hour with PBS plus 1% bovine serum albumin (BSA). The plates were stored at −20° C. in BSA containing buffer until required. Samples of hybridoma culture supernatant (50 μl/well) were incubated with hgp580 for 1 hour at room temperature.

The plates were washed three times with PBS plus 0.05% BSA. Biotinylated-goat/rat-IgG (Vector Labs., Burlingame, Calif.) diluted 1/1000 in PBS plus 1% BSA, was added (50 μl/well), and incubated with the cells for 1 hour at 25° C. The plates were washed three times followed by the addition of streptavidin bridging reagent (50 μl/well) diluted 1/1000 in PBS plus 1% BSA (Bethesda Research Laboratories, Inc. Gaithersburg, Md.), was added to each well and incubated for 45 minutes at 25° C. The plates were washed six times with PBS plus 0.05% BSA and bound antibody was quantitated using O-phenylenediamine (1 mg/ml) dissolved in 0.1M citrate buffer, pH 4.5, to which 0.012% hydrogen peroxide was added, (100 μl/well). After a 15 minute incubation in the dark, absorbance at 450 nm was determined using a Titertek Multiscanner (Flow Laboratories). In all assays, Y3Ag1.2.3 culture supernatant was used as a negative control. Supernatants were considered positive if they possessed absorbance equal to or greater than two standard deviations above background. Hybridomas from positive wells were cloned twice by limiting dilution using irradiated rat fibroblasts as feeder cells.

Additional immunoassays used $^{125}$I-labeled affinity purified antibodies to rat F(ab')$_2$ (Dr. C. J. Dean Chester Beatty Research Institute Sutton, Surrey, England). 50 μl dilutions of monoclonal antibodies were incubated for 1 hour at 4° C. with monolayers of viable cells, or at 25° C. with fixed cells, grown to confluence on 96 well microtest plates. Bound monoclonal antibody was quantitated after thorough washing by incubation with $5 \times 10^5$ cpm/well of $^{125}$I-labeled sheep/rat F(ab')$_2$ for 1 hour at either 4° C. (viable cells), or 25° C. (fixed cells). The cells were washed with medium and lysed with 200 μl of 2N NaOH. Radioactivity was determined by counting in a Beckman model 8000 gamma counter.

Purification and Radiolabeling of Monoclonal Antibodies. Monoclonal antibodies were isolated from culture supernatants by affinity chromatography after concentration by ammonium sulfate (40% saturation) precipitation. The anti-rat K chain MAb, Mark 1, (H. Bazin, Brussels, Belgium) was linked to Affigel-10 (10 mg protein/ml beads) using the manufacturer's instructions and used to purify positive monoclonal antibodies. Elution of monoclonal antibodies from the absorbent column was achieved with 3M potassium thiocyanate, and fractions (1 ml) were collected and immediately neutralized with 0.1M Hepes buffer, pH 8.0. Monoclonal antibodies were assayed for purity by polyacrylamide gel electrophoresis in sodium dodecyl sulfate (SDS PAGE), and when required, radiolabeled with $^{125}$Iodine (ICN Pharmaceutical Inc., Irvine, Calif.) by the chloramine T method, specific activity of approximately 2 uCi/ug.

Immunoblotting. Immuno blots were carried out essentially by the method of Towbin et al (1979) *P.N.A.S.*, 76: 4350 using the modifications already described. Proteins were electrophoretically transferred overnight from 2–17.5% DATD cross linked, denaturing polyacrylamide gradient gels to nitrocellulose paper at 50 volts and 0.29 amps. Antigen was detected using the Vectastain alkaline phosphatase procedure according to the manufacturer's instructions (Vector Labs, San Francisco, Calif.).

Immunoperoxidase Procedure. Tissue samples (human and rat) were snap frozen in liquid $N_2$ and then stored at $-20°$ C. until required; 4 um cryostat section were used in a the immumoperoxidase staining procedures. The protocol followed was the Vectastain ABC anti rat IgG procedure (Vector Laboratories, San Francisco, Calif.) with diaminobenzidine as substrate (1 mg/ml in Tris-HCl, pH 7.2) diluted 1:1 with 0.02% hydrogen peroxide.

b. Exemplary Anti-Human gp580 Monoclonal Antibodies

Table VI demonstrates a sampling of positive hybridoma clones which have been generated against either rgp580 or hgp580 and which exhibit immunoreactivity against the hgp580 antigen. Based on its high titer of antibody production, clone HGR1:69 was selected for antibody characterization studies.

Hybridoma clones HGR1:69 (ATCC deposit no. HB9041) and GP21:56 (ATCC deposit no. HB9046) were deposited with the American Type Culture Collection on Mar. 20, 1985 under the Budapest Treaty.

TABLE VI

| HYBRIDOMA CLONES | | |
|---|---|---|
| Immunogen | Monoclonal Antibody | Specificity |
| rat gp580 | rat GP21:56 | rat and human gp580 |
| human gp580 | rat HGR1:69 | rat and human gp580 |
| human gp580 | rat HGR1:70 | human gp580 |
| human gp580 | mouse HGM1:4 | human gp580 |
| human gp580 | mouse HGM1:9 | human gp580 |
| human gp580 | mouse HGM1:34 | human gp580 |
| human gp580 | mouse HGM1:39 | human gp580 |
| human gp580 | mouse HGM1:43 | human gp580 |
| human gp580 | mouse HGM1:47 | human gp580 |
| human gp580 | mouse HGM1:54 | human gp580 |
| human gp580 | mouse HGM1:60 | human gp580 |
| human gp580 | mouse HGM1:77 | human gp580 |
| human gp580 | mouse HGM1:78 | human gp580 |
| human gp580 | mouse HGM1:84 | human gp580 |

EXAMPLE V:

Detection of Human Tumors

Monoclonal antibodies produced in accordance with the procedures set forth above may successfully be utilized in assay protocols for the identification and detection of suspected human tumors. In general, immunodiagnostic protocols are well known to those skilled in the art. These monoclonal antibody immunodetection systems of the present invention may conveniently be adapted to detect tumor cells in a variety of sample types. For example, the presence of the tumor antigen hgp580, may be detected in aqueous samples such as blood, urine, sweat, serum, plasma, plural effusions or ascitic fluid and may be accomplished by one of numerous immunodetection techniques generally known in the art, for example, radioimmunoassays ("RIA's") and enzyme-linked immunosorbent assays ("ELISA's"). Alternatively, tumor cells present in solid tissues such as human tissue biopsies, may be detected using well known immunohistological assays.

a. Proposed Solid Phase Radioimmunoassay for the Quantification and Detection of gp580 in Aqueous Samples The presence of circulating hgp580 may prove to be a valuable diagnostic indicator of either the presence of a tumor somewhere in the patient's body, or alternatively, as a diagnostic tool for following the progression of chemotherapy or onset of a relapse. The following protocol is a suggested approach for utilizing the monoclonal antibodies of the present invention for the detection and quantification of circulating hgp580 antigens in aqueous samples.

A preferred embodiment of the aqueous sample assay utilizes a standard radioimmuno-assay approach for the quantification of hgp580 antigen. Briefly, immunobeads are prepared by linking affinity purified monoclonal antibodies to Affi-Gel 10 (1 ml. Affi-Gel 10 with 20 mg. protein) by following the manufacturers instructions. Immunobeads prepared in this manner are used to initially bind all of the hgp580 present in a given sample aliquot.

To perform this initial binding of hgp580 from a sample aliquot, the immunobeads (10 μl packed volume) along with 100 μl of RIA buffer (0.5% bovine serum albumin, 0.19% Triton X-100, 0.02% azide in DPBS, pH 7.4), standard antigen dilutions (or aqueous samples such as serum samples from patients), 100 μl of normal human serum and protease inhibitors are mixed together in 1.5 ml polystyrene tubes. The binding is completed by rotating the tubes overnight at 4° C. followed by washing the antigen-loaded immunobeads six times with RIA buffer.

The amount of hgp580 bound by the immunobeads may then be quantified utilizing, for example, a biotinylated monoclonal antibody preparation and radiolabeled streptavidin, taking advantage of the avidin/-biotin reaction. Briefly, biotinylated monoclonal antibodies are prepared by reacting the monoclonal antibody (1 mg/ml in 0.1M Hepes, pH 8.0) with 1 mg/ml D-biotin N-hydroxyl succinimide ester ("NHS-biotin") in anhydrous DMSO for 4 hours at 0° C. at a NHS-biotin: monoclonal antibody ratio of 1:8 (v/v). After biotinylation is complete, the biotinylated antibodies may be freed of NHS and uncoupled biotin by ultrafiltration with a Centrifree Micropartition Unit and YM-30 membranes. A useful washing buffer is 100 mM Hepes and 0.05% azide, pH 8.0.

Ten micrograms of biotinylated antibodies is added to the antigen-loaded and washed immunobeads, and incubated for 4 hours at room temperature. The immunobeads are then washed 6 times with RIA buffer and incubated for an additional 4 hours with 5 μg of $^{125}$I-streptavidin, washed 6 times with RIA buffer and bound radioactivity is determined in an autogamma counter. Iodination of the streptavidin may conveniently be carried out by the chloramine-T method. By comparing standard curves developed with known antigen concentrations to those developed with patient samples, the concentration of hgp580 present in the patient sample can be determined.

b. Detection of hgp580 Antigen on Human Tissue Biopsies

Monoclonal antibodies of the present invention may also be successfully utilized to detect the presence of tumor cells in human tissue biopsies. In a preferred embodiment, tumor tissue samples are frozen in liquid nitrogen and stored in air-tight containers at −20° C. until required. Preferably, cryostat sections, approximately 4 um thick, are used in all immunohistological assays. The preferred assay protocol used in the Vectastatin ABC anti-rat IgG or anti-mouse IgG procedures, both of which are well known to those skilled in the art, using either horseradish peroxidase or alkaline phosphatase as the enzyme marker.

Briefly, the tissue sections are fixed in acetone and endogenous enzyme activity inhibited using either 0.3% $H_2O_2$ in methanol (for peroxidase staining) or 20% acetic acid (for phosphatase staining). Antibody (supernatant, ascites or affinity purified) is layered on the slide, incubated for 1 hour, washed, and the tissues incubated for 30 minutes with biotinylated anti-rat (or mouse) IgG according to the manufacturer's instructions. Avidin-enzyme complex is then layered on the slide after thorough washing with buffer, and incubated with the tissue for 1 hour. At this time the appropriate enzymes substrates are prepared. The tissues are washed and incubated with the enzyme for 5 to 30 minutes, washed and counterstained with Mayer's hematoxylin. The presence of tumor cells in the biopsy tissue is indicated by the appearance of a positive enzyme reaction which is observable microscopically on the slide.

Table VII displays results which have been obtained from screening various tissue samples in the above manner utilizing either a representative monoclonal antibody developed against rgp580 (GP21:56) or one developed against hgp580 (HGR1:69). Antibodies prepared against either the rat or human antigen appear to function equally well in the identification of human tumors. It will be further appreciated by those skilled in the art that these monoclonal antibodies exhibit a preference for tumors of breast origin and, in particular, metastatic tumors having a breast tissue origin.

TABLE VII

| | Immuno-Screening of Various Tissues | |
|---|---|---|
| | Monoclonal Antibody No. of Positives/Total No. Tested | |
| Tumor | HGR1:69 | GP21:56 |
| Infiltrating Ductal Breast Carcinoma | 4/8 | 3/8 |
| Normal Breast | 0/5 | 0/5 |
| Lymph Node Metastasis (Breast) | 2/2 | 2/2 |
| Lung Metastasis (Breast) | 2/2 | 2/2 |
| Brain Metastasis (Breast) | 1/2 | 1/2 |
| Colon Carcinoma | 0/3 | 0/3 |
| Normal Colon | 0/1 | 0/1 |
| Liver Metastasis (Colon) | 0/1 | 0/1 |
| Benign Colon Tumor | 0/1 | 0/1 |
| Melanoma | 0/1 | 0/1 |

EXAMPLE VI:

Antibodies To gp580 as Inhibitors of Tumor Colonization and Metastases

Rat tumor assays were devised to demonstrate the efficacy of the monoclonal antibodies of the present invention in preventing or inhibiting the lung colonization and spontaneous metastases of tumor cells. In one assay, affinity purified GP21:56 was injected intravenously into the jugular vein of metofane-anesthetized rates (100 μg/rat), 24 hours before injecting $10^6$ MTLn3 cells subcutaneously into the mammary fat pad of each rat. At the same time as tumor cells were injected, each rat was given an additional 100 ug of antibody intravenously into the jugular vein.

The tumor was allowed to grow in vitro for 30 days, during which time antibody was administered intravenously at a concentration of 50 μg/rat, three times a week. After 30 days the animals were sacrificed by inhalation of metofane, and examined macroscopically for the presence of overt metastases in the lung, inguinal and lumbar lymph nodes, kidneys and thymus. An antibody which doesn't cross-react with gp580 was used in the control group.

TABLE VIII

| | Effect of MAb on Spontaneous Metastasis of 13762NF Clone MTLn3 cells Injected s.c. | | | | | |
|---|---|---|---|---|---|---|
| Anti-gp580 MAb Treatment* | Av. Tumor Dia (mm) | No. Rats with Metastases/ Total No. Rates at d 30 | | | | |
| | | Lung | Inq. LN | Lumb. LN | Renal | Thymus |
| Control | 17.92 | 6/6 | 6/6 | 5/6 | 0/6 | 2/6 |
| GP21:56 | 20.13 | 1/6 | 4/6 | 3/6 | 1/6 | 0/6 |

*F344 rats received 50 μg MAb 3× week 3 days after s.c. injection of $10^6$ MTLn3 cells.

As demonstrated by the results in Table VIII, an antibody directed against the tumor-associated protein, gp580, significantly decreased the occurrence of spontaneous metastases. In a similar study, the antibodies ability to prevent lung colonization by injected tumor cells was tested. F344 rats were anesthetized by metofane inhalation and 50 ug of affinity purified MAb was injected intravenously into the jugular vein of each rat. Immediately after injection of MAb, $5 \times 10^4$ MTLn3 cells were injected i.v. into the jugular vein. The animals were sacrificed 23–30 days later, and each animal were examined for overt metastases. The amount of tumor present in the lung of each animal was determined by counting the number of visible tumor colonies in each lung. The appropriate non-reactive MAbs were used as controls. Monoclonal antibody MT10:21 is a monoclonal antibody which does not react with gp580.

However, it is thought that this antibody may react with other metastases-associated antigens.

TABLE IX

Effect of MAb on Experimental Metastasis of 13762 NF Clone MTLn3 Cells Injected I.V.

| Anti-gp580 MAb Treatment* | No. Lung Tumor Colonies (Range) at d 30 | | | | | | |
|---|---|---|---|---|---|---|---|
| Control | >250, | >250, | >250, | >250 | >250 | >250 | (>250) |
| GP21:56 | 14, | 23, | 26, | 27, | 72, | 110 | (14-110) |
| MT10:21 | 21, | 24, | 25, | 45, | 126, | 150 | (21-150) |

*F344 rats received 50 μg MAb i.v. before injection i.v. of 5 × 10⁴ MTLn3 cells.

The data displayed in Table IX again demonstrates the potential usefulness in reducing spontaneous metastases, particularly those to the lung. Such a finding further raises the possibility of utilizing such antibodies as, for example, adjuvants to cancer surgery, which some oncologists feel, promote the dislocation of metastic tumors. Additionally, such antibodies and the gp580 antigen could lead to the development of immunization protocols for preventing metastases.

Although the present invention is described in terms of specific embodiments, those of skill in the art will understand that the techniques utilized are generally, well known methods with numerous variations and embodiments. Suitable variations will be apparent to those of skill in the art. For example, although the present monoclonal antibodies are primarily described in terms of rat/rat hybrids, mouse/mouse hybrids are similarly suitable as illustrated by Table VI. Similarly, skilled molecular biologists and protein biochemists will recognize that numerous variations in the protein isolation techniques disclosed may be employed for the successful isolation of gp580. All such variations are considered to be within the scope of the present invention and the appended claims.

What is claimed is:

1. An isolated, purified human gp580 (hgp580) antigen having the following properties:
   (a) an apparent molecular weight of approximately 550 kilodaltons upon sodium dodecyl sulfate-polyacrylamide gel electrophoresis;
   (b) isolatable from cell membrane fractions of metastatic mammary tumor cells;
   (c) substantially resistant to treatment with trypsin or hyaluronidase; and
   (d) substantially sensitive to treatment with pronase;
   (e) substantial binding to peanut agglutinin following treatment with neuraminidase.

2. The hgp580 antigen of claim 1, having approximately the following number of each of the indicated amino acid residues for every 1000 amino acid residues of the glycoprotein:

| Aspartic Acid | 120 |
|---|---|
| Threonine | 87 |
| Serine | 166 |
| Glutamic Acid | 154 |
| Proline | 37 |
| Glycine | 78 |
| Alanine | 26 |
| Cysteine | not detected |
| Valine | 65 |
| Methionine | not detected |
| Leucine | 56 |
| Isoleucine | 38 |
| Tyrosine | 23 |
| Phenylalanine | 29 |
| Histidine | 11 |
| Lysine | 94 |
| Arginine | 16 |
| Glucosamine | 147 |
| Galactosamine | 113 |

3. The hgp580 antigen of claim 1, prepared by a process comprising:
   (a) extracting soluble proteins including gp580 from a metastatic mammary tumor which contains the gp580;
   (b) subjecting the extractate to gel exclusion chromatography;
   (c) collecting the excludate;
   (d) subjecting the excludate to anionic exchange chromatography;
   (e) eluting the fractions which bind to the anionic exchange resin;
   (f) subjecting the eluent to gel exclusion chromatography;
   (g) collecting the excluded fractions.

4. The antigen of claim 3 wherein step (a) comprises extracting a human metastatic mammary tumor with a solution which includes 4M guanidine HCl; step (b) comprises subjecting the extractate to Sphadex G-50 chromatography in a buffer which includes 8M urea; step (d) comprises subjecting the excludate to DEAE-Sephacel in a buffer which includes 8M urea; and step (f) comprises subjecting the eluant to Sepharose Cl-2B chromatography in a buffer which includes 4M guanidine HCl.

5. The hgp580 antigen of claim 1, prepared by a process comprising;
   (a) extracting soluble proteins including gp580 from a metastatic mammary tumor which contains the gp580;
   (b) subjecting the extractate to gel exclusion chromatography;
   (c) collecting the excludate;
   (d) subjecting the excludate to density gradient centrifugation;
   (e) fractionating the equilibrated density gradient;
   (f) subjecting the gp580-containing fractions to gel exclusion chromatography; and
   (g) collecting the excluded fractions.

6. The antigen of claim 5 wherein step (a) comprises extracting a human metastatic mammary tumor with a solution which includes 4M guanidine-HCl; step (b) comprises subjecting the extractate to Sephadex G-50 chromatography; step (d) comprises subjecting the excludate to cesium chloride buoyant density gradient centrifugation and step (f) comprises subjecting the gp580-containing fractions to Sepharose Cl-2B chromatography in a buffer which includes 4M guanidine HCl.

7. A method for preparing an essentially pure hgp580 antigen useful in the production of human tumor-directed antibodies comprising:

(a) extracting hgp580 from a metastatic mammary tumor with a solution which includes 4M guanidine HCl;
(b) subjecting the extractate to Sephadex G-50 chromatography in a buffer which includes 8M urea;
(c) collecting the excludate;
(d) subjecting the excludate to DEAE-Sephacel in a buffer which includes 8M urea;
(e) eluting the fractions which bind to the DEAE-Sephacel;
(f) subjecting the eluant to Sepharose CL-2B chromatography in a buffer which includes 4M guanidine HCl; and
(g) collecting the excluded fractions.

8. A method for preparing an essentially pure rgp580 antigen, useful in the production of antibodies capable of reacting with human tumors, comprising the steps of:
(a) extracting rgp580 from a metastatic mammary tumor with a solution which includes 4M guanidine-HCl;
(b) subjecting the extractate to Sephadex G-50 chromatography;
(c) collecting the excludate;
(d) subjecting the excludate to cesium chloride buoyant density gradient centrifugation;
(e) fractionating the equilibrated density gradient;
(f) subjecting the rgp580 containing fractions to Sepharose CL-2B chromatography in a buffer which includes 4M guanidine-HCl; and
(g) collecting the excluded fractions.

9. An antibody to hgp580 antigen.

10. An antibody to rat gp580 (rgp580) antigen.

11. The antibody of claim 9 or 10 wherein the antibody is further defined as a monoclonal antibody.

12. The antibody of claim 11 wherein the monoclonal antibody is a rat monoclonal antibody.

13. The antibody of claim 12 wherein the rat monoclonal antibody is further defined as GP21:56 (ATCC Deposit No. HB9042).

14. The antibody of claim 12 wherein the rat monoclonal antibody is further defined as HGR:69 (ATCC Deposit No. HB9041).

15. A diagnostic method for detecting the presence of metastatic human tumor cells in a sample which comprises the steps of:
(a) contacting the sample with an antibody as defined by claim 9 or 10; and
(b) detecting antigen specifically bound by the antibody, the presence of such an antigen in the sample being indicative of metastatic tumor cells therein.

16. The method of claim 15 wherein the sample comprises a body fluid and the method further comprises:
(a) admixing a sample which includes the body fluid with the antibody under conditions which will promote specific antigen/antibody interactions; and
(b) detecting a specific antigen/antibody interaction, such an interaction being indicative of the presence of metastatic tumor cells in the sample.

17. The method of claim 15 wherein the sample comprises a body tissue and the method further comprises:
(a) layering a sample which includes the tissue with the antibody;
(b) incubating the layered sample under conditions which will promote specific antigen/antibody interactions; and
(c) detecting a specific antigen/antibody interaction, such an interaction being indicative of the presence of metastatic tumor cells in the sample.

18. A hybrid continuous cell line producing an antibody to hgp580 antigen

19. The cell line of claim 18 wherein the cell line corresponds to ATCC deposit HB9041 or HB9042.

20. A hybrid continuous cell line producing an antibody to rpg580 antigen.

21. A method for reducing the frequency of metastatic mammary carcinoma tumor lesions in a patient comprising parenterally administering to the patient a therapeutically effective amount of a composition which comprises an antibody to a gp580 antigen.

22. The method of claim 21 wherein the gp580 antigen is rgp580.

23. The method of claim 21 wherein the gp580 antigen is hgp580.

24. The method of claim 21 wherein the antibody is GP21:56 (ATCC Deposit No. HB9041).

25. The method of claim 21 wherein the antibody is HGR1:69 (ATCC Deposit No. HB9041).

26. A kit for the detection of cancer in humans comprising:
(a) an antibody to gp580 antigen;
(b) an immunoreaction detection reagent; and
(c) means for containing said antibody and immunodetection reagent.

27. A kit for the detection of cancer in humans comprising:
(a) a gp580 antigen
(b) an immunoreaction detection reagent; and
(c) means for containing said antigen and immunodetection reagent.

28. The kit of claim 26 or 27, wherein the immunoreaction detection reagent is an enzyme-linked antigen or antibody.

29. The kit of claim 26 or 27 wherein the immunoreaction detection reagent is a radio-labeled antigen or antibody.

* * * * *

UNITED STATES PATENT AND TRADEMARK OFFICE
CERTIFICATE OF CORRECTION

Page 1 of 2

PATENT NO. : 5,030,559
DATED : July 9, 1991
INVENTOR(S) : Garth L. Nicholson, Peter A. Steck and Susan M. North It is certified that error appears in the above-identified patent and that said Letters Patent is hereby corrected as shown below:

In Claim 3, line 31, column 32, insert "and" after chromatography;

In Claim 4, line 35, column 32, delete "4M" and insert therefor "4 M".

In Claim 4, line 36, column 32, delete "Sphadex" and insert therefor "Sephadex".

In Claim 4, line 37 and in line 39, column 32, delete "8M" and insert therefor "8 M".

In Claim 4, line 41, column 32, delete "4M" and insert therefor "4 M".

In Claim 6, line 64, column 32, delete "C1-2B" and insert therefor "CL-2B".

UNITED STATES PATENT AND TRADEMARK OFFICE
CERTIFICATE OF CORRECTION

PATENT NO. : 5,030,559

DATED : July 9, 1991

INVENTOR(S) : Garth L. Nicholson et al

It is certified that error appears in the above-identified patent and that said Letters Patent is hereby corrected as shown below:

In claim 14, line 41, column 33, delete "HGR:69" and insert therefor "HGR1:69".

In Claim 24, line 33, column 34, delete "HB9041" and insert therefor "HB9042".

Signed and Sealed this

Fifteenth Day of December, 1992

Attest:

DOUGLAS B. COMER

*Attesting Officer*    Acting Commissioner of Patents and Trademarks